United States Patent
Kato et al.

(10) Patent No.: US 10,711,273 B2
(45) Date of Patent: Jul. 14, 2020

(54) AMINO ACID-MODIFIED NUCLEIC ACID AND UTILIZATION THEREOF

(71) Applicant: NATIONAL INSTITUTE OF ADVANCED INDUSTRIAL SCIENCE AND TECHNOLOGY, Tokyo (JP)

(72) Inventors: Yoshio Kato, Tsukuba (JP); Naoshi Kojima, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 15/579,841

(22) PCT Filed: Jun. 8, 2016

(86) PCT No.: PCT/JP2016/067025
§ 371 (c)(1),
(2) Date: Dec. 5, 2017

(87) PCT Pub. No.: WO2016/199801
PCT Pub. Date: Dec. 15, 2016

(65) Prior Publication Data
US 2018/0251759 A1    Sep. 6, 2018

(30) Foreign Application Priority Data
Jun. 9, 2015  (JP) .................................. 2015-116992

(51) Int. Cl.
| | | |
|---|---|---|
| C12N 15/113 | (2010.01) | |
| C12N 15/09 | (2006.01) | |
| C12N 15/67 | (2006.01) | |
| C12N 9/00 | (2006.01) | |

(52) U.S. Cl.
CPC .............. *C12N 15/113* (2013.01); *C12N 9/00* (2013.01); *C12N 15/09* (2013.01); *C12N 15/67* (2013.01); C12N 2310/111 (2013.01); C12N 2310/12 (2013.01)

(58) Field of Classification Search
None
See application file for complete search history.

(56) References Cited

U.S. PATENT DOCUMENTS

| | | |
|---|---|---|
| 2003/0082575 A1 | 5/2003 | Schultz et al. |
| 2003/0108885 A1 | 6/2003 | Schultz et al. |
| 2008/0153745 A1 | 6/2008 | Tian |
| 2009/0281280 A1 | 11/2009 | Suga et al. |
| 2010/0087677 A1 | 8/2010 | Tian |
| 2013/0068108 A1 | 3/2013 | Rivera |
| 2013/0217599 A1 | 8/2013 | Suga |

FOREIGN PATENT DOCUMENTS

| | | |
|---|---|---|
| EP | 2647720 A1 | 10/2013 |
| EP | 2647720 A9 | 10/2013 |
| JP | 2004-537984 | 12/2004 |
| JP | 2009-504182 | 2/2009 |
| WO | WO 2007/066627 | 5/2009 |
| WO | WO 2012/026566 | 3/2012 |

OTHER PUBLICATIONS

Wang L, et al., Addition of the keto functional group to the genetic code of *Escherichia coli*, Proc Natl Acad Sci USA, Jan. 7, 2003, vol. 100, No. 1, p. 56-61.
Masahiko Shishido, "An Approach towards Synthetic Microorganism from BioMacromolecular Chemistry", Kobunshi, 2002, vol. 51, pp. 438 to 441.
Watanabe S, et al., Interactions Between Petides Containing Nucleobase Amino Acids and T7 Phages Displaying S. cerevisiae Proteins, Biopolymers, 2007, vol. 88, No. 2, p. 131-140.
Supplementary Search Report, European Patent Application No. 16807507.5, dated Feb. 13, 2019, 14 pages.
Rumit M et al. Protein synthesis with ribosomes selected for the incorporation of (beta)-amino acids. Biochemistry. May 2015; 54(23): 3694-3706.
Ohuchi M et al. The flexizyme system: A highly flexible tRNA aminoacylation tool for the translation apparatus. Current Opinion in Chemical Biology. Oct. 2007; 11(5): 537-542.
Office Action, Japanese Patent Application No. 2017-523668, dated Jan. 15, 2019, and English machine translation, 9 pages.
Diederichsen, Ulf, "Pairing Properties of Alanyl Peptide Nucleic Acids Containing an Amino Acid Backbone with Alternating Configuration", Angew. Chem., 35:445-448 (1996).
Gaj, Thomas et al., "ZFN, TALEN, and CRISPR/Cas-based methods for genome engineering", Trends Biotechnol., 31:397-405 (2013).
Garner, Philip et al., "a-Helical Peptide Nucleic Acids (rPNAs): A New Paradigm for DNA-Binding Molecules", J. Am. Chem. Soc., 122:2405-2406 (2000).
Ito, Kenichiro et al., "An artificial restriction DNA cutter for site-selective gene insertion in human cells", Chem. Commm., 49:6764-6766 (2013).
Nielsen, Peter et al, "Sequence-Selective Recognition of DNA by Strand Displacement with a Thymine-Substituted Polyamide", Science, 254:1497-1500 (1991).
Roviello, Giovanni et al., "Evidences for supramolecular organization of nucleopeptides: synthesis, spectroscopic and biological studies of a novel dithymine L-serine tetrapeptide", Mol. BioSyst., 7:1073-1080 (2011).

(Continued)

*Primary Examiner* — Channing S Mahatan
(74) *Attorney, Agent, or Firm* — Myers Bigel, P.A.

(57) ABSTRACT

Provided is a method for synthesizing a protein, into which a nucleobase amino acid (NBA) is introduced at a desired position, that comprises: a step for preparing mRNA into which a modified codon is inserted at a desired position downstream of an initiation codon; and a step for translating the aforesaid mRNA into a protein in the presence of tRNA, said tRNA recognizing the modified codon and being acylated with the NBA. Also provided is a ribozyme that catalyzes the aminoacylation of tRNA and comprises two RNA molecules.

13 Claims, 10 Drawing Sheets
Specification includes a Sequence Listing.

(56) References Cited

OTHER PUBLICATIONS

Ura, Yasuyuki, et al. "Self-Assembling Sequence-Adaptive Peptide Nucleic Acids", Science, 325:73-77 (2009).
Yamazaki, Takahisa et al., "Dinucleotide-Analogous Tetrapeptides, Specific Triplex Formation with Complementary Polynucleotides", Tetrahedron Lett., 38:8363-8366 (1997).

(a) GENERAL FORMULA  (b) AlaT-CME  (c) HalT-CME

FIG. 8
(a)
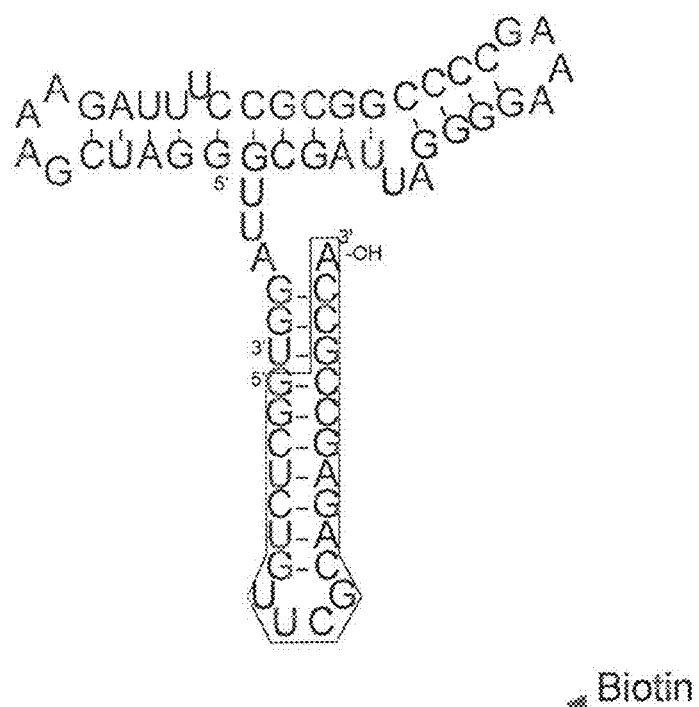
(b)
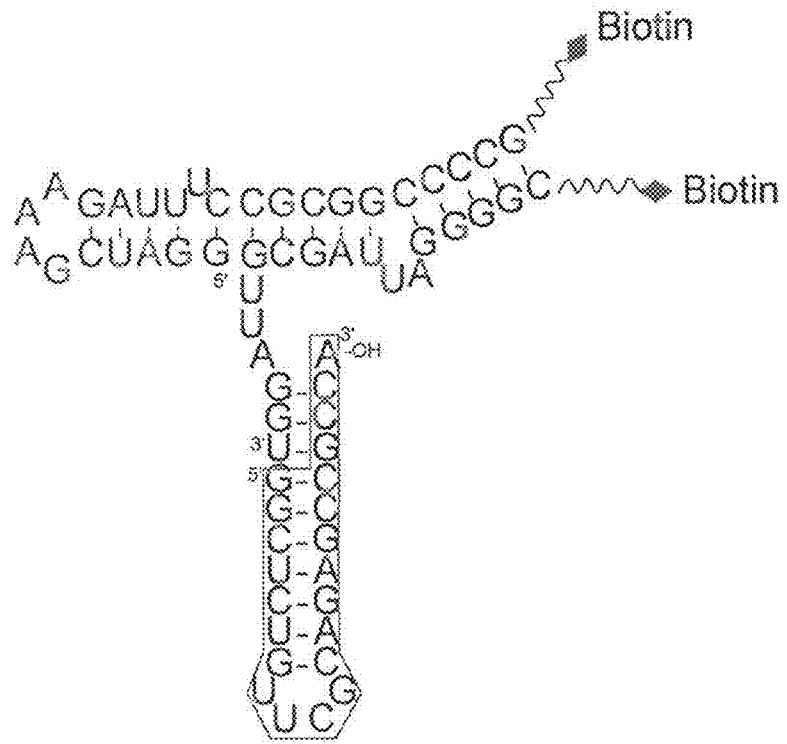

FIG. 11
(a)
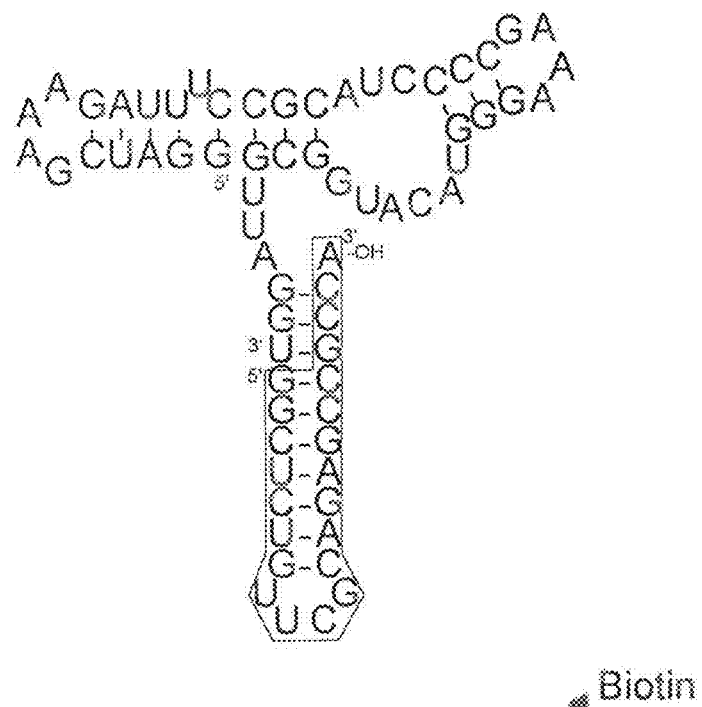
(b)
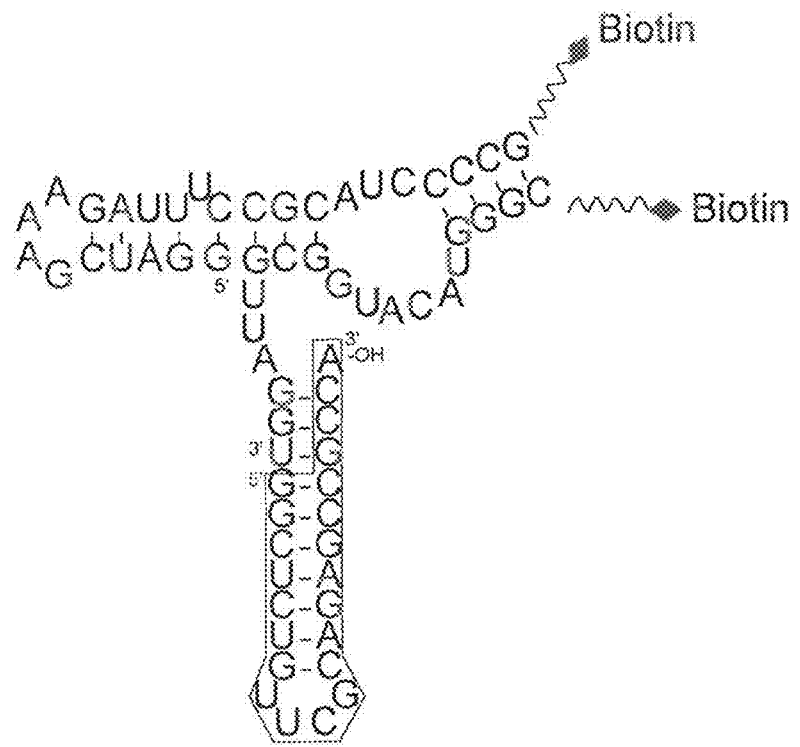

AMINO ACID-MODIFIED NUCLEIC ACID AND UTILIZATION THEREOF

STATEMENT OF PRIORITY

This application is a 35 U.S.C. § 371 national phase application of International Application Serial No. PCT/JP2016/067025, filed Jun. 8, 2016, which claims the benefit, under 35 U.S.C. § 119 (a) of Japanese Patent Application No. 2015-116992, filed Jun. 9, 2015, the entire contents of each of which are incorporated by reference herein.

STATEMENT REGARDING ELECTRONIC FILING OF A SEQUENCE LISTING

A Sequence Listing in ASCII text format, submitted under 37 C.F.R. § 1.821, entitled 5576-343_ST25.txt, 3045 bytes in size, generated Dec. 13, 2017 and filed via EFS-Web, is provided in lieu of a paper copy. This Sequence Listing is hereby incorporated herein by reference into the specification for its disclosures.

TECHNICAL FIELD

The present invention relates to a method and to a protein synthesis system for synthesizing a protein into which a nucleobase amino acid (NBA) is introduced at a desired position.

BACKGROUND ART

Since the 1990s, genome projects for various organisms have been conducted, and the entire genomic nucleotide sequence has already been determined in many species of organism, including humans. Currently, post-genomic studies such as the functional analyses of proteins encoded by individual genes are eagerly being conducted using the results of the genome analyses. In particular, studies using genetically modified animals are essential in analyzing how a particular gene functions in the living body at the individual level, and they have gained an important position since new therapeutic agents can be developed by using genetically modified animals as disease model animals. Therefore, many genetically modified animals such as transgenic animals, in which particular exogenous genes have been introduced, and gene-knockout animals, in which particular endogenous genes have been disrupted, have been developed.

Recently, much attention has been focused on genome editing as a technique for knocking out target genes in various species of organism. Genome editing is a technique for introducing a mutation at a particular site into a target gene by using an artificial nuclease (e.g., ZFN or TALEN) or an RNA-directed nuclease (e.g., CRISPR/Cas) that can recognize and cleave any target sequence in a DNA chain (Non-Patent Document 1). The artificial nuclease such as ZFN or TALEN is a chimeric protein in which a DNA binding domain that specifically recognizes a target sequence and a DNA cleavage domain of the restriction enzyme FokI are linked, whereas, in the CRISPR/Cas system, a small RNA molecule, referred to as the guide RNA (gRNA), recognizes a target sequence and the RNA dependent DNA nuclease Cas9 cleaves the DNA. Since designing and synthesis of RNA that specifically recognizes a target sequence are much easier than those of protein, the CRISPR/Cas system is an increasingly attractive genome editing tool.

Molecules that can specifically recognize and bind to a DNA sequence include peptide nucleic acids (PNAs), in addition to DNA and RNA. PNAs are unnatural nucleic acid analogs that are artificially produced to have properties similar to DNA and RNA, and have a peptide backbone that replaces the deoxyribose-phosphate backbone in DNA. Advantages of PNA are, for example, the following. (1) The PNA/DNA double-strand or the PNA/RNA double-strand can be formed stably without being affected by pH or salt concentration because PNAs have no negative charges derived from phosphate groups present in DNA and RNA and are neutral. (2) PNAs have extremely high specificity of nucleotide sequence recognition because the decrease in the Tm value of PNA is greater than those in DNA or RNA. (3) PNAs are suitable for use in cells because they are highly resistant to the degradation with nucleases and proteases in vivo. Therefore, various PNAs having a peptide backbone have been developed (Non-Patent Documents 2 to 7).

Focusing on the above advantages of the PNA, genome editing using PNA has also been attempted. For example, Komiyama et al. at the University of Tokyo have succeeded in disrupting a target gene by introducing a PNA that specifically binds to the target gene and a cerium ion into cells by electroporation (Non-Patent Document 8). In this method, the double strand of DNA at a target site is unwound by intercalating PNA oligomers into the double-stranded DNA adjacent to the target site, and the single-stranded target site is cut with using a cerium ion. PNAs have extremely high specificity of nucleotide sequence recognition and therefore they are specifically inserted at the target site. However, a cerium ion may cut single-stranded DNAs other than the single-stranded DNA formed by the insertion of the PNAs, resulting in a problem of poor specificity. Thus, there are high expectations for artificial nucleases having high specificity for any target sequence as a useful genome editing tool, by fusing a nuclease domain consisting of a protein and a target DNA binding domain consisting of PNAs.

However, all PNAs have been produced by chemical synthesis thus far. The synthesis of PNA oligomers is conducted by solid-phase synthesis similar to the peptide synthesis by repeating the condensation of monomers protected with Boc, Cbz, Fmoc, or the like and deprotection. Therefore, in the solid-phase synthesis, the yield of 10-mer PNA oligomers would be as low as about 35% even if the efficiency of one condensation reaction was 90%, and thus the efficient production of long chain PNAs is extremely difficult. Furthermore, when chemically synthesized PNAs are fused with a protein, the problem is that the fusion with PNAs may not be sufficient or excessive PNAs are fused, depending on the nature of the protein. Alternatively, a PNA and a protein can be continuously synthesized by a chemical method; however, enzyme proteins such as nucleases are usually composed of 100 amino acids or more, and it is therefore substantially impossible to synthesize enzyme proteins at a practical level in consideration of the problem of reaction efficiency in the solid-phase synthesis method as described above. Therefore, establishing a process that makes it possible to synthesize a PNA-protein fusion by a process other than chemical synthesis is expected to provide a big advantage in post-genomic studies.

Puromycin, blasticidin, and the like, are known as naturally occurring NBAs or analogs thereof, and they are used as antibiotics because they inhibit the process of translation and inhibit the protein synthesis by binding to the ribosome. Therefore, it has been considered to be difficult to synthesize proteins introduced with PNAs containing NBAs as constituent units by a ribosomal translation system.

CITATION LIST

Non-Patent Document

Non-Patent Document 1: Gaj et al., Trends Biotechnol., Vol. 31, pp. 397-405 (2013)
Non-Patent Document 2: Nielsen et al., Science, Vol. 254, pp. 1497-1500 (1991)
Non-Patent Document 3: Garner et al., J. Am. Chem. Soc., Vol. 122, pp. 2405-2406 (2000)
Non-Patent Document 4: Roviello et al., Mol. BioSyst., Vol. 7, pp. 1073-1080 (2011)
Non-Patent Document 5: Ura et al., Science, Vol. 325, pp. 73-77, (2009)
Non-Patent Document 6: Diederichsen, Angew. Chem. Vol. 35, pp. 445-448 (1996)
Non-Patent Document 7: Yamazaki et al., Tetrahedron Lett., Vol. 38, pp. 8363-8366 (1997)
Non-Patent Document 8: Ito et al., Chem. Commun. Vol. 49, pp. 6764-6766, (2013)

SUMMARY OF INVENTION

Technical Problem

It is an object of the present invention to provide a method for solving various problems of the prior art and for synthesizing a protein into which an NBA is introduced.

Solution to Problem

The present inventors have confirmed for the first time as a result of diligent studies that NBA-acylated tRNAs are incorporated into ribosomes and NBA-introduced proteins are synthesized by the ribosomal translation. It is a surprising discovery, overturning previous assumptions that NBA-acylated tRNAs are incorporated into ribosomes without inhibiting the translation process and NBA-introduced proteins are synthesized. The present inventors succeeded in establishing a method for synthesizing a protein into which an NBA is introduced at a desired position with a ribosomal translation system based on this novel discovery.

Thus, according to one embodiment, the present invention provides a method for synthesizing a protein into which an NBA is introduced at a desired position, comprising the steps of: providing an mRNA having a modified codon inserted at a desired position downstream of a start codon; and translating the mRNA into a protein in the presence of a tRNA acylated with a nucleobase amino acid (NBA) and recognizing the modified codon.

Preferably, the method further comprises the step of preparing the tRNA acylated with the NBA with a ribozyme that catalyzes the aminoacylation reaction of a tRNA.

Moreover, according to one embodiment, the present invention provides a cell-free protein synthesis system for synthesizing a protein into which an NBA is introduced at a desired position, comprising: (1) a nucleobase amino acid (NBA), (2) a tRNA that recognizes a modified codon, and (3) a ribozyme that catalyzes the aminoacylation reaction of the tRNA.

The ribozyme is preferably an enhanced flexizyme.

The ribozyme preferably consists of one or more RNA molecules having no 5'-terminal phosphate group.

The ribozyme preferably consists of two RNA molecules.

The two RNA molecules are preferably (1)
(SEQ ID NO: 4)
GGAUCGAAAGAUUUCCGCGGCCCCG
and (2)
(SEQ ID NO: 5)
CGGGGAUUAGCGUUAGGU.

The modified codon is preferably an amber codon.

Moreover, according to one embodiment, the present invention provides a ribozyme consisting of the following two RNA molecules:
(1) GGAUCGAAAGAUUUCCGCGGCCCCG (SEQ ID NO: 4) and
(2) CGGGGAUUAGCGUUAGGU (SEQ ID NO: 5) or consisting of two RNA molecules modified from the RNA molecules (1) and (2) by a substitution, a deletion, or an addition of 1 to 3 bases at the 3' terminus of the RNA molecule (1) and/or the 5' terminus of the RNA molecule (2).

Moreover, according to one embodiment, the present invention provides a ribozyme consisting of the following two RNA molecules:
(3) GGAUCGAAAGAUUUCCGCAUCCCG (SEQ ID NO: 7) and
(4) CGGGUACAUGGCGUUAGGU (SEQ ID NO: 8) or consisting of two RNA molecules modified from the RNA molecules (3) and (4) by a substitution, a deletion, or an addition of 1 to 3 bases at the 3' terminus of the RNA molecule (3) and/or the 5' terminus of the RNA molecule (4).

The 5' terminus and/or the 3' terminus of the two RNA molecules are preferably biotinylated.

Advantageous Effects of Invention

The method for synthesizing a protein and the cell-free protein synthesis system according to the present invention make it possible to synthesize a protein introduced a nucleobase amino acid (NBA) at a desired position easily and with high efficiency.

Moreover, the ribozyme that catalyzes the aminoacylation reaction of a tRNA according to the present invention is useful because the ribozyme according to the present invention consists of two RNA molecules and therefore can be prepared easily and at low cost by chemical synthesis. Furthermore, since the ribozyme that catalyzes the aminoacylation reaction of a tRNA according to the present invention can be chemically synthesized, it can be biotinylated easily, and thereby, it becomes possible to improve the purification efficiency of aminoacylation reaction products.

BRIEF DESCRIPTION OF DRAWINGS

FIG. 8 is a schematic drawing of (a) a full length eFx (SEQ NO:1 and SEQ NO:3) and (b) a split eFx (SEQ ID NO 4, SEQ ID NO:5 and SEQ ID NO:3).

FIG. 11 is a schematic drawing of (a) a full length dFx (SEQ ID NO:9 and SEQ ID NO:3 and (b) a split dFx (SEQ ID NO:7, SEQ ID NO:8 and SEQ ID NO:3).

DESCRIPTION OF EMBODIMENTS

The present invention will be described in detail below, however the present invention is not limited to the embodiments described herein.

Figure 1:
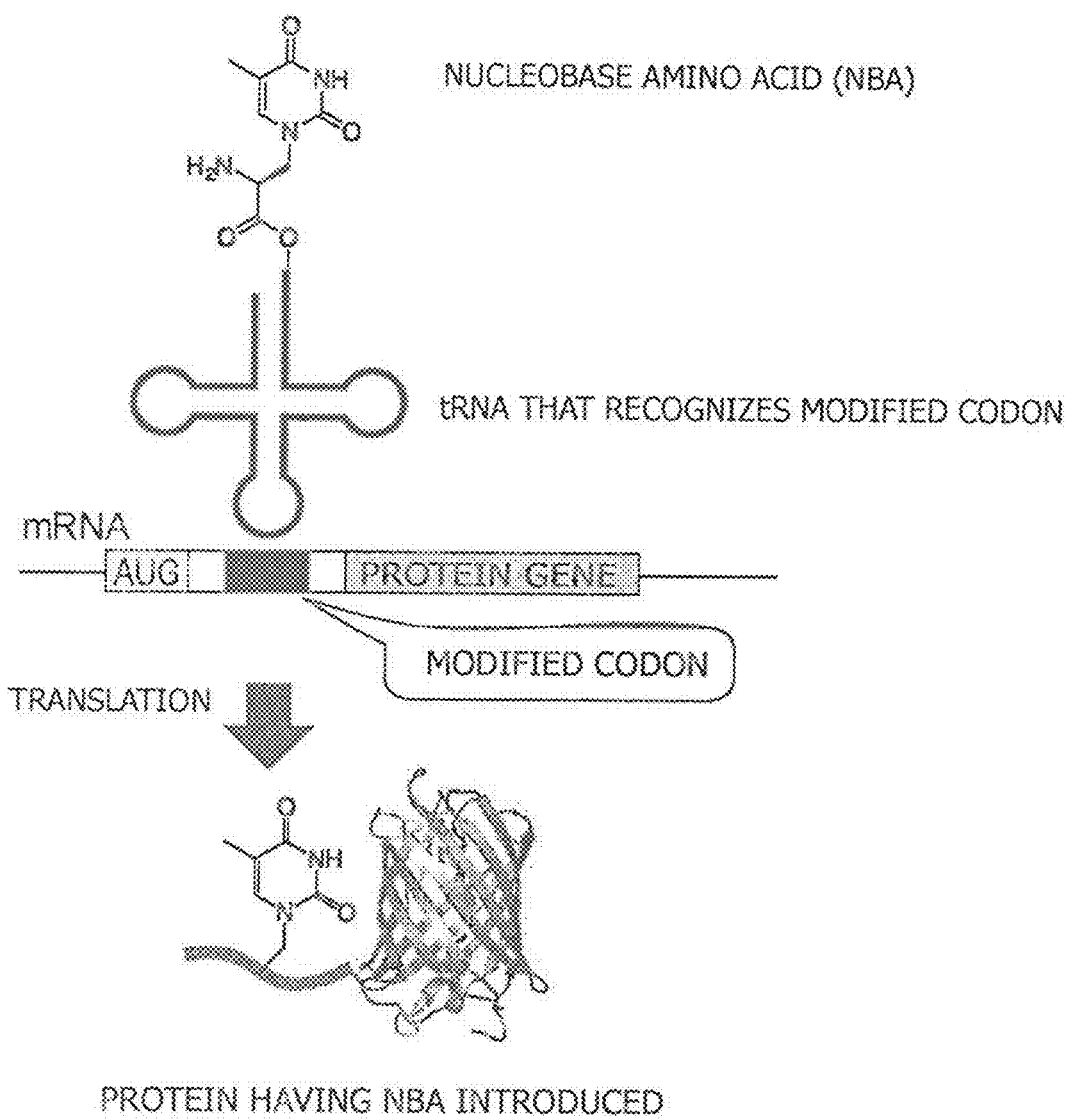
FIG. 1 is a schematic drawing illustrating a method for translating and synthesizing a protein into which a nucleobase amino acid (NBA) is introduced at a desired position.

According to the first embodiment, the present invention is a method for synthesizing a protein into which an NBA is introduced at a desired position, comprising the steps of: providing an mRNA having a modified codon inserted at a desired position downstream of a start codon; and translating the mRNA into a protein in the presence of a tRNA acylated with a nucleobase amino acid (NBA) and recognizing the modified codon. A schematic drawing of a method for synthesizing a protein according to the present embodiment is illustrated in FIG. 1.

In the method for synthesizing a protein according to the present embodiment, an mRNA encoding a protein of interest in which a modified codon is inserted at a desired position is prepared and used.

The "mRNA" in the present embodiment may be any mRNA comprising a sequence encoding a protein of interest and a sequence necessary for ribosome to start the protein translation (e.g., Shine-Dalgarno (SD) sequence, Kozak sequence, or internal ribosomal entry site (IRES)). Moreover, the protein of interest may be any protein, for example, a nuclease, a recombinase, an integrase, a deaminase, a methyl transferase, a sulfotransferases, or a glycosylase.

The mRNA having a modified codon inserted may be prepared by producing a DNA encoding the mRNA having a modified codon inserted, and transcribing the DNA into mRNA with RNA polymerase. The modified codon can be inserted into DNA, for example, by a well-known gene recombinant technique such as PCR.

Examples of the "modified codon" that may be used in the present embodiment include the three stop codons: an amber codon, an ochre codon, or an opal codon, to which no amino acid is assigned in the natural world; 4-base codons or 5-base codons (Hosaka et al., Nucl. Acids Res., Vol. 29, pp. 3646-3651, 2001); and artificial codons using unnatural bases such as s-y or Ds-Px (Hirao et al., Nat. Biotech., Vol. 20. pp. 177-182, 2002; Hirao, TCI Mail, Vol. 148, pp. 2-15, 2010). Alternatively, since leucine, serine, or arginine is each encoded with six codons, some of them can be assigned to a modified codon. Moreover, a plurality of different modified codons selected from those described above can be used in combination (Rodriguez et al., Proc. Natl. Acad. Sci., Vol. 103, pp. 8650-8655, 2006), and several kinds of NBAs can thereby be introduced into a protein of interest. One or more modified codons may be inserted into mRNA at any one or more positions downstream of the start codon of the mRNA.

The modified codon used in the present embodiment is preferably a stop codon and particularly preferably an amber codon. Normally, the amber codon is recognized by the translation termination factor RF1 to terminate the protein translation with ribosome; however, artificial addition of tRNA having an anticodon (CUA) to the amber codon (amber suppressor tRNA) aminoacylated with any of amino acids allows the introduction of the amino acid at the position corresponding to the amber codon and continuation of translation of the downstream part in the gene. More specifically, in the method for synthesizing a protein according to the present embodiment, use of the amber suppressor tRNA aminoacylated with a nucleobase amino acid (NBA) allows the modification of the amber codon into a codon defining the NBA and the synthesis of a protein into which an NBA is introduced at a desired position in the protein of interest.

Then, a tRNA acylated with a nucleobase amino acid (NBA) and recognizing the modified codon is prepared.

The "tRNA" used in the present embodiment may be a natural tRNA derived from any organism or an artificial modified tRNA constructed to have an anticodon to a modified codon. The modified tRNA may be prepared by producing a DNA encoding the modified tRNA and transcribing the DNA in vitro, similar to the preparation of the mRNA having the modified codon inserted, as disclosed above.

The "nucleobase amino acid (NBA)" used in the present embodiment may be any amino acid having a nucleobase as its side chain.

Examples of the nucleobases composing the NBAs that may be used in the present embodiment include adenine (A), guanine (G), cytosine (C), thymine (T), uracil (U), and derivatives thereof. Examples of the derivatives of nucleobases include 5-methylcytosine, 5-hydroxymethylcytosine, 7-deazaguanine, 4-thiouracil, 2-aminopurine, hypoxanthine, and 8-oxoguanine. A preferred nucleobase in the present embodiment is thymine (T) or uracil (U).

Examples of the amino acid composing the NBA that may be used in the present embodiment include 20 natural amino acids and derivatives thereof. Examples of the derivatives of amino acids include homoalanine, alanine, norvaline, beta-alanine, gamma-aminobutyric acid, aminoethyl glycine, aminomalonic acid, aspartic acid, and glutamic acid. A preferred amino acid in the present embodiment is alanine or homoalanine.

The NBAs in the present embodiment can be synthesized by conventionally known methods of chemical synthesis or methods of chemical synthesis described in the following Examples and other methods of chemical synthesis corresponding thereto. Moreover, the NBAs in the present embodiment can be bio-synthesized using enzymes such as serine acetyltransferase or acetylserine sulfhydrylase.

Figure 4:
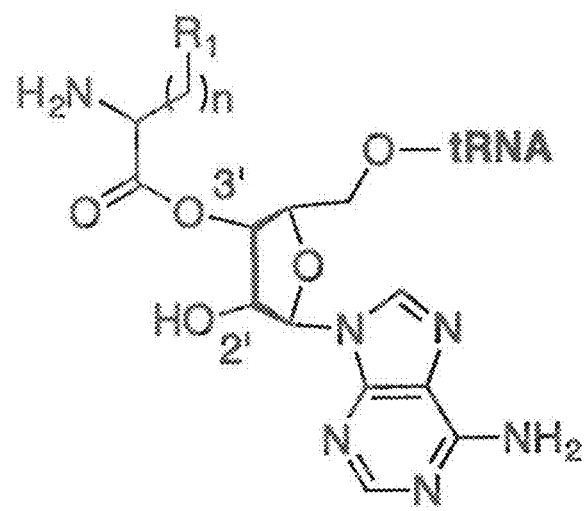
FIG. 4 illustrates the chemical structure of aminoacylated tRNAs.
Figure 5:
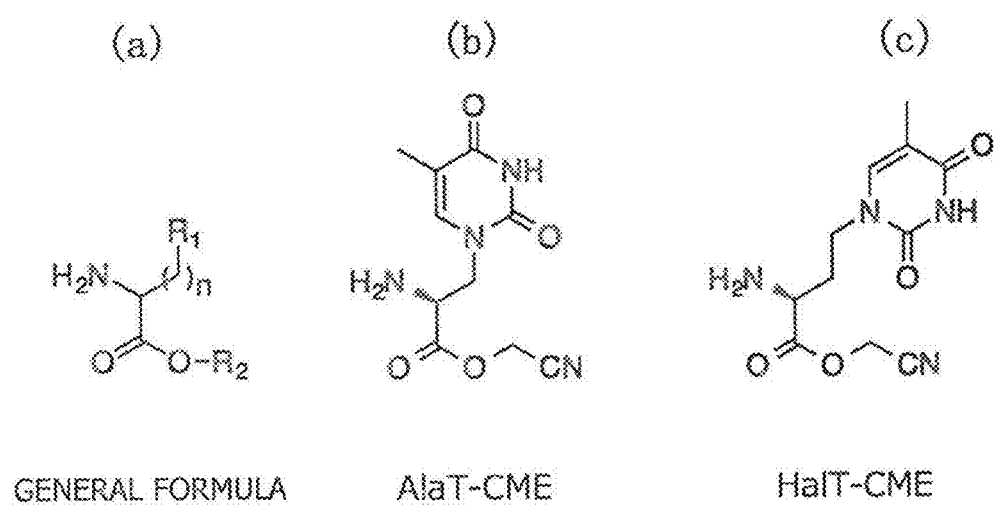
FIG. 5 illustrates the chemical structure of nucleobase amino acid (NBA)-aminoacylated tRNAs.

The general formulae of "NBA-acylated tRNAs" in the present embodiment are illustrated in FIG. 4 and FIG. 5 (a). In the formula, $R_1$ is a nucleobase or a derivative thereof, $R_2$ is RNA, and n is the number of atoms in the linker and an integer of 1 to 10, preferably an integer of 1 to 5, and particularly preferably an integer of 1 to 3. Moreover, the atoms composing the linker may be carbon, nitrogen, oxygen, sulfur, phosphorus, boron, or the like and preferably carbon or nitrogen.

The "NBA-acylated tRNAs" in the present embodiment may be NBA-acylated at either 2'-OH or 3'-OH of the ribose in tRNA, similarly to tRNAs acylated with a natural amino acid. FIG. 4 illustrates a tRNA aminoacylated at 3'-OH.

The "NBA-acylated tRNA" in the present embodiment can be prepared by a conventionally known method, and examples include a method involving use of flexizyme, which is a ribozyme that catalyzes the aminoacylation reaction of a tRNA (Murakami et al., Nat. Meth., Vol. 3, pp. 357-359, 2006); a method involving condensation of a one base-deletion variant or two base-deletion variant of a tRNA and an aminoacylated RNA monomer or RNA dimer, with an enzyme (e.g., RNA ligase) that catalyzes the formation of the phosphodiester linkage (Heckler et al., Biochemistry, Vol. 23, pp. 1468-1473, 1984, Noren et al., Science, Vol. 244, pp. 182-188, 1989): and a method involving use of a mutant of aminoacylation tRNA synthetase (Wang et al., Science. Vol. 292, pp. 498-500, 2001).

The NBA-acylated tRNA in the present embodiment is preferably prepared by using a flexizyme. Since the flexizyme recognizes only 3'-terminal region of tRNA and interacts with none of the anticodon region, the D arm region, the TΨC region, and the like (Xiao et al., Nature, Vol. 454, pp. 358-361, 2008), tRNA from a wider range of species of organism, including tRNA having a deletion of the D arm region or the TΨC region, can be used (Martins & Schimmel, tRNA, ASM Press, Soll and RajBhandary (Eds.), pp, 349-370, 1995).

In addition to the original form of flexizyme (Fx), examples of the flexizymes include a dinitrobenzyl flexizyme (dFx), an enhanced flexizyme (eFx), and an amino flexizyme (aFx). Any of them may be used in the present embodiment, but the flexizyme is preferably eFx (SEQ ID NO: 1).

Since the flexizyme is a ribozyme, it may be prepared by in vitro transcription or by chemical synthesis, similarly to the mRNA and tRNA. Based on the result of X-ray crystallographic analysis, it has been thought that interaction between the 5'-terminal phosphate group of the flexizyme and magnesium ion is important for the aminoacylation activity of the flexizyme (Xiao et al., Nature, Vol. 454, pp. 358-361, 2008, Suga et al., Met. Ion Life Sci., Vol. 9, pp. 175-196, 2011) and therefore it has conventionally been thought that the preparation of the flexizyme by in vitro transcription is preferred. However, the flexizyme actually has the aminoacylation activity regardless of the presence or absence of the 5'-terminal phosphate group as confirmed in the following Examples. Therefore, the ribozyme in the present embodiment is preferably prepared by chemical synthesis and thus preferably consists of one or more RNA molecules having no 5'-terminal phosphate group.

When the flexizyme is chemically synthesized, the flexizyme preferably consists of two RNA molecules. The flexizyme is composed of approximately 45-base RNA. By dividing this into the first RNA molecule composed of approximately 25 bases and the second RNA molecule composed of approximately 20 bases and chemically synthesizing them, it is possible to prepare the flexizyme at high efficiency and low cost.

For example, when an eFx is divided into two RNA molecules, the eFx may be separated between C24 and G29 so as to maintain the double stranded structure formed of cytosines (C22 to C24) at the position 22 to 24 and guanines (G29 to G31) at the position 29 to 31 in eFx. Since this double stranded structure is shared among all flexizymes, dFx and aFx can be divided similarly by separating them at one of the positions corresponding to those between C24 to G29 in eFx.

Accordingly, the flexizyme in the present embodiment preferably consists of the first RNA molecule composed of GGAUCGAAAGAUUUCCGCGGCCCCG (SEQ ID NO: 4) and the second RNA molecule composed of CGGGGAUUAGCGUUAGGU (SEQ ID NO: 5).

Moreover, the flexizyme may have a substitution, a deletion, or an addition of one to several bases at the 3' terminus of the first RNA molecule and/or the 5' terminus of the second RNA molecule as long as the double stranded structure of the flexizyme is conserved. The "one to several" is preferably "1 to 3", "1 or 2", or "1". Moreover, the 3' terminus of the first RNA molecule and/or the 5' terminus of the second RNA molecule may be modified with a label compound such as biotin.

Then, the mRNA having the modified codon inserted is translated into a protein in the presence of an NBA-acylated tRNA. The translation of the mRNA into the protein may be conducted with a cell-free protein synthesis system in vitro or with the protein synthesis system in living cells. The translation of the mRNA into the protein in the present embodiment is preferably conducted with a cell-free protein synthesis system.

The translation with a cell-free protein synthesis system in vitro can be conducted by adding an aminoacylated tRNA and an mRNA having a modified codon inserted into the cell-free protein synthesis system reconstituted by mixing various factors necessary for translation such as ribosome and translation factors (Shimizu et al., Nat. Biotech., Vol. 19, pp. 751-755, 2001). The cell-free protein synthesis system can be prepared from an extract from prokaryotic cells such as *Escherichia coli* or eukaryotic cells such as rabbit reticulocytes by a conventionally known process. Moreover, the cell-free protein synthesis system is commercially available as a kit, and such a commercially available kit may be used. Examples of such a commercially available kit include PUREsystem (a product made by New England Biolab Inc.).

When the amber codon is used as a modified codon, a cell-free protein synthesis system not containing the translation termination factor RF1 or a cell-free protein synthesis system to which an anti-RF1 antibody (Agafonov et al., FEBS Lett., Vol. 579, pp. 2156-2160, 2005) or an aptamer that binds to RF1 (Sando et al., Bioorg. Med. Chem. Lett., Vol. 17, pp. 1216-1220, 2007) is added may be used. In this way, it is possible to increase the efficiency of, not terminating translation, but alternatively introducing NBA into a protein when the ribosome reaches the amber codon on the mRNA.

When a 4-base codon is used as a modified codon, a cell-free protein synthesis system to which Ribo-Q (Neumann et al., Nature, Vol. 464, pp. 441-444, 2010), which is a ribosome modified to have a preference for the 4-base codon, is added as the ribosome may be used.

When some of the codons that encode leucine, serine, or arginine are assigned to one or more modified codons, a cell-free protein synthesis system may be prepared by, for example, treating a cell extract by the solid-phase probe method (Tsurui et al., Anal. Biochem., Vol. 221, pp. 166-172, 1994) and eliminating or isolating one or more particular tRNAs.

When translation is performed using the protein synthesis system in living cells, the protein of interest can be synthesized, for example, by injecting by microinjection or introducing by lipofection an aminoacylated tRNA and an mRNA having a modified codon inserted to living cells such as *Xenopus* oocytes or mammalian cells (Nowak et al., Science. Vol. 268, pp. 439-442, 1995).

According to the second embodiment, the present invention is a cell-free protein synthesis system for synthesizing a protein into which an NBA is introduced at a desired position, comprising: (1) a nucleobase amino acid (NBA), (2) a tRNA that recognizes a modified codon, and (3) a ribozyme that catalyzes the aminoacylation reaction of the tRNA.

The "cell-free protein synthesis system" of the present embodiment may be prepared by adding the (1) to (3) to a cell-free protein synthesis solution reconstituted by mixing various factors necessary for translation such as ribosome and translation factors. In the present embodiment, the "cell-free protein synthesis solution" means a solution in which a protein can be synthesized by adding mRNA and DNA of the gene encoding the protein of interest. The cell-free protein synthesis solution may be prepared from an extract from prokaryotic cells or eukaryotic cells by a conventionally known process or a cell-free protein synthesis solution included in a commercially available cell-free protein synthesis kit may be used.

The "nucleobase amino acid" (NBA), the "tRNA that recognizes a modified codon", the "ribozyme that catalyzes the aminoacylation reaction of a tRNA", and the "mRNA having a modified codon inserted" in the present embodiment are as defined in the first embodiment and may be prepared as described above.

In the cell-free protein synthesis system of the present embodiment, similarly to the method in the first embodiment, an enhanced flexizyme (eFx) is preferably used as the ribozyme that catalyzes the aminoacylation reaction of a tRNA, and the use of eFx consisting of the first RNA molecule composed of GGAUCGAAAGAUUUCCGCGGCCCCG (SEQ ID NO: 4) and the second RNA molecule composed of CGGGGAUUAGCGUUAGGU (SEQ ID NO: 5) is particularly preferred. The flexizyme may have a substitution, a deletion, or an addition of one to several bases at the 3' terminus of the first RNA molecule and/or the 5' terminus of the second RNA molecule as long as the double stranded structure of the flexizyme is conserved. The "one to several" is preferably "1 to 3", "1 or 2", or "1". Moreover, the 5' terminus and/or the 3' terminus of the RNA molecules may be modified with a label compound such as biotin.

In the cell-free protein synthesis system of the present embodiment, similarly to the method in the first embodiment, the modified codon used may be one of the three stop codons: an amber codon, an ochre codon, or an opal codon; a 4-base codon or a 5-base codon; an artificial codon with an unnatural base; or the like. Alternatively, some of the codons that encode leucine, serine, or arginine may be assigned to modified codons. The modified codon in the present embodiment is preferably a stop codon and particularly preferably an amber codon. As described above, the component of the cell-free protein synthesis solution may be changed as appropriate to be optimized depending on the modified codon to be used.

The cell-free protein synthesis system of the present embodiment may be provided as a cell-free protein synthesis kit by combining the system with an additional component, e.g., an expression vector, a nucleic acid, an amino acid, an energy source, a buffer solution, a container used in the protein synthesis, or an instruction, as appropriate. When the cell-free protein synthesis system of the present embodiment is provided as a cell-free protein synthesis kit, (1) a nucleobase amino acid (NBA), (2) a tRNA that recognizes a modified codon, and (3) a ribozyme that catalyzes the aminoacylation reaction of the tRNA may be in a state in which they are added to a cell-free protein synthesis solution beforehand or may be prepared to add the (1) to (3) to the cell-free protein synthesis solution when used.

The method for synthesizing a protein in the first embodiment and the cell-free protein synthesis system in the second embodiment make it possible to synthesize a protein having a nucleobase, which has been conventionally difficult to synthesize easily and at high efficiency.

According to the third embodiment, the present invention is a ribozyme that catalyzes the aminoacylation reaction of a tRNA, wherein the ribozyme consists of the following two RNA molecules:

(1)
(SEQ ID NO: 4)
GGAUCGAAAGAUUUCCGCGGCCCCG and (2)
(SEQ ID NO: 5)
CGGGGAUUAGCGUUAGGU.

According to the fourth embodiment, the present invention is a ribozyme that catalyzes the aminoacylation reaction of a tRNA, wherein the ribozyme consists of the following two RNA molecules:

(3)
(SEQ ID NO: 7)
GGAUCGAAAGAUUUCCGCAUCCCCG and (4)
(SEQ ID NO: 8)
CGGGUACAUGGCGUUAGGU.

The ribozymes of the third and fourth embodiments are not only those consisting of the particular sequences described above, but may have a substitution, a deletion, or an addition of one to several bases at the 3' terminus of the first RNA molecule ((1) or (3)) and/or the 5' terminus of the second RNA molecule ((2) or (4)) as long as the secondary structure of the ribozyme is conserved. The "one to several" is preferably "1 to 3", "1 or 2", or "1".

The ribozymes of the third and fourth embodiments may be prepared by in vitro transcription or by chemical synthesis. Since the ribozymes in the present embodiments are composed of two short RNAs, they can be prepared easily and at low cost by chemical synthesis and preferably prepared by chemical synthesis.

The ribozymes of the third and fourth embodiments are preferably modified with a label compound such as biotin at the 5' terminus and/or the 3' terminus of the two RNA molecules. The 3' terminus of the first RNA molecule ((1) or (3)) and/or the 5' terminus of the second RNA molecule ((2) or (4)) are particularly preferably biotinylated. The biotinylation can be performed by a conventionally known process.

The ribozymes of the present embodiments may be generally used in aminoacylation reactions of tRNAs, and may be used, not only in the aminoacylation of tRNAs with NBAs, but also in the aminoacylation of tRNAs with any natural or unnatural amino acids.

The ribozymes of the present embodiments are useful since they may be prepared easily and at low cost by chemical synthesis. Moreover, a label compound is also easily introduced, and it is therefore possible to improve the purification efficiency after the aminoacylation reaction of a tRNA.

EXAMPLES

The present invention will further be described with reference to Examples described below. The present invention is not limited thereto.

1. Synthesis of Nucleobase Amino Acid (NBA)

Figure 2:
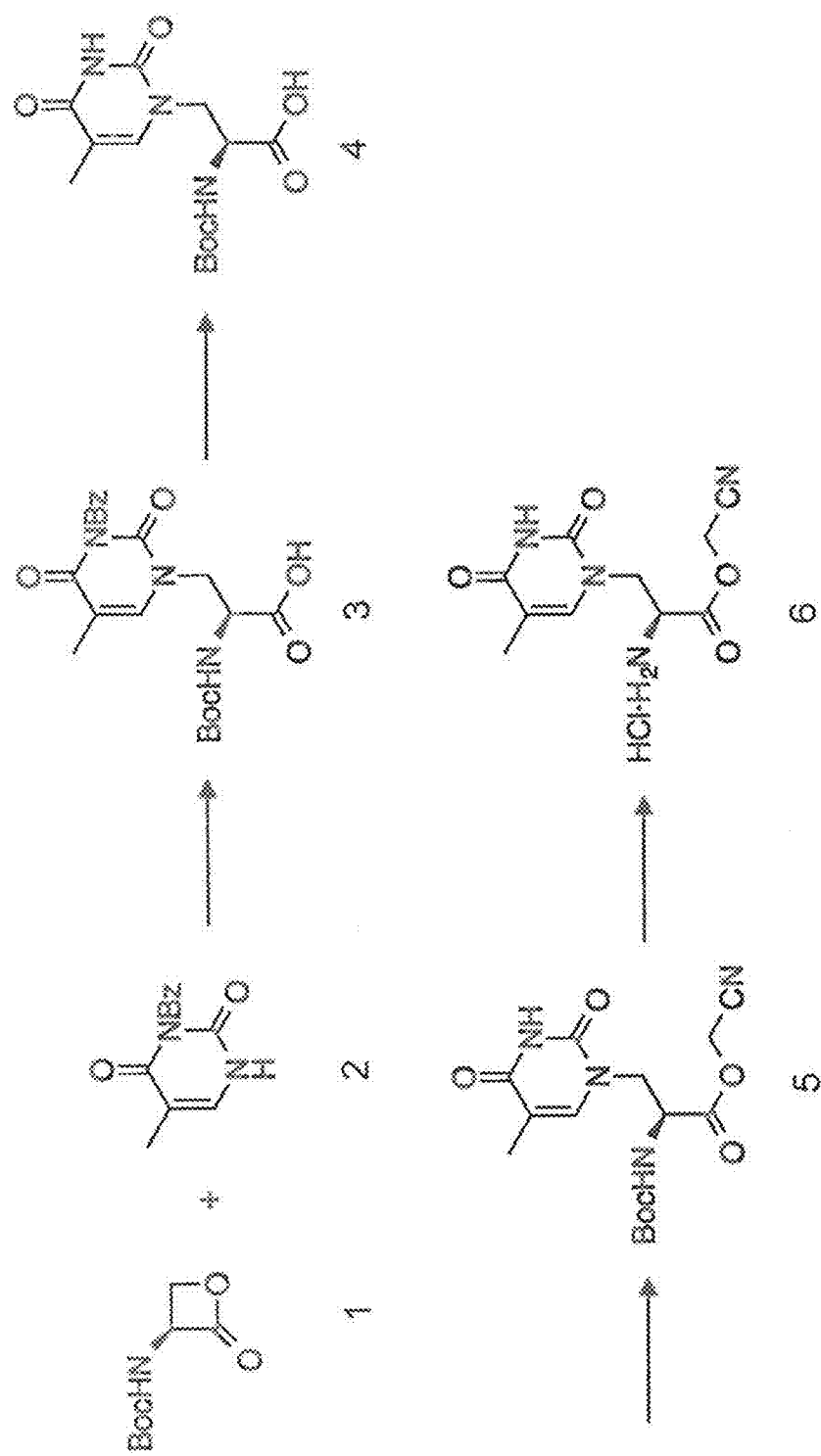
FIG. 2 illustrates a synthetic scheme of a cyanomethyl ester derivative of alanyl-thymine (AlaT-CME).
Figure 3:
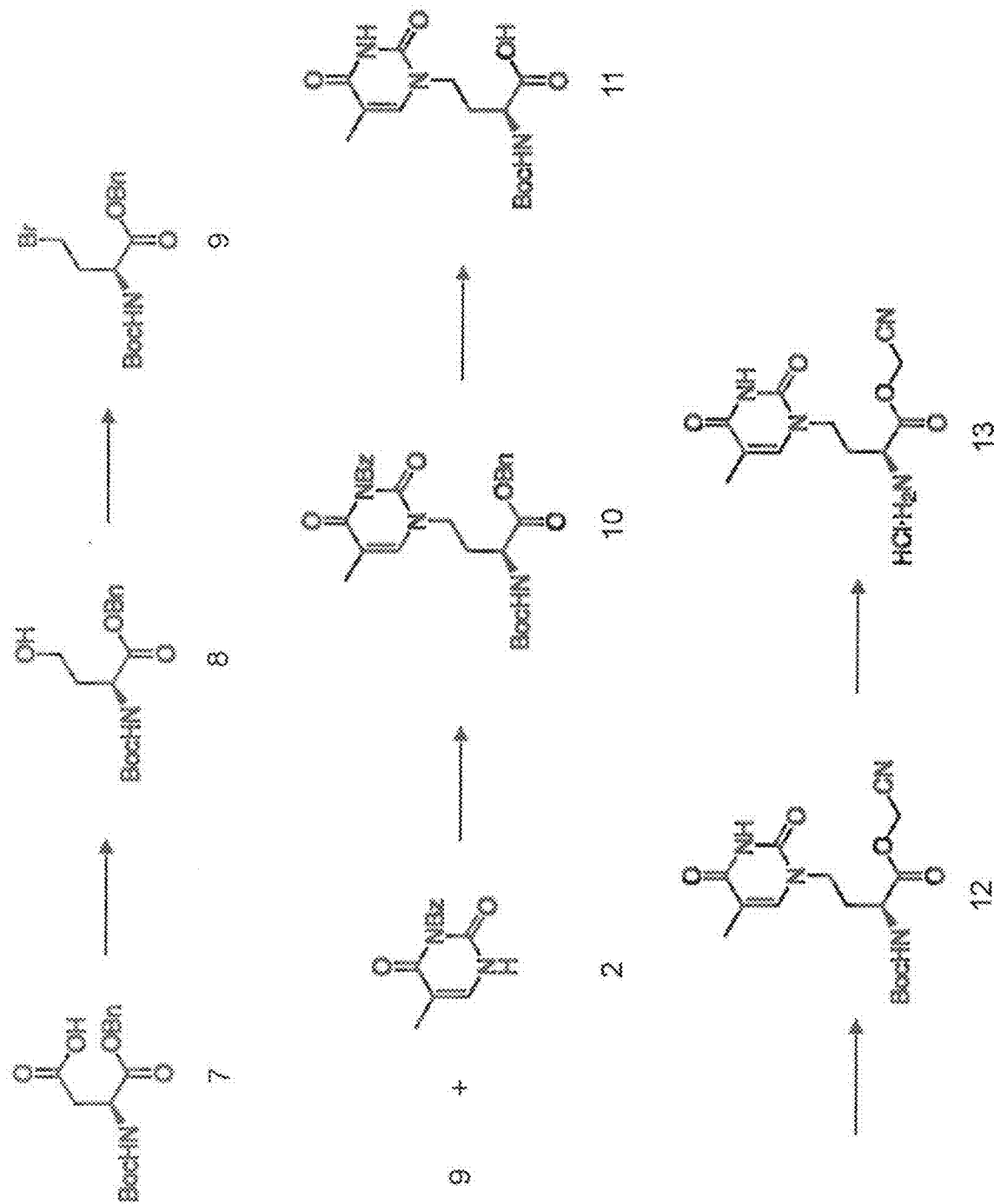
FIG. 3 illustrates a synthetic scheme of a cyanomethyl ester derivative of homoalanyl-thymine (HalT-CME).

A cyanomethyl ester derivative (Compound 6) of alanyl-thymine (AlaT) and a cyanomethyl ester derivative of homoalanyl-thymine (HalT) were obtained by the procedure described below. Respective synthetic schemes are illustrated in FIG. 2 and FIG. 3.

1-1. Synthesis of (S)-β-(1-thyminyl)alanine Cyanomethyl Ester Hydrochloride (AlaT Cyanomethyl Ester Derivative: Compound 6)

(1) Synthesis of (S)—N-tert-butoxycarbonyl-β-(N3-benzoyl-1-thyminyl)alanine (Compound 3)

Under an argon atmosphere, N3-benzoylthymine (Compound 2) (1.84 g, 8.0 mmol) was dissolved in dimethylformamide (80 mL) and diazabicycloundecene (DBU, 1.20 mL, 8.0 mmol) was slowly added dropwise at room temperature with stirring. After stirring the reaction solution at room temperature for 10 minutes, a dimethylformamide solution (40 mL) of N-tert-butoxycarbonylserine β-lactone (Compound 1) (1.43 g, 7.64 mmol) was slowly added dropwise. After further stirring the reaction solution at room temperature for 2.5 hours, acetic acid (0.46 mL, 8.0 mmol) was added. The reaction solution was concentrated under reduced pressure and the residue was boiled with toluene twice. The resulting residue was purified by silica gel column chromatography (elution solvent: chloroform-ethanol) and 2.36 g (74%) of the title compound (Compound 3) was obtained as a white foam.

$^1$H NMR (500 MHz, DMSO-$d_6$) δ: 13.17 (br s, 1H, COOH), 8.02 (d, 2H, Bz, J=7.6 Hz), 7.79 (m, 1H, Bz), 7.59-7.56 (m, 3H, H-6, Bz), 7.26 (br d, 1H, NH, J=9.1 Hz), 4.42 (m, 1H, CH), 4.31 (m, 1H, CH$_2$a), 3.62 (m, 1H, CH$_2$b), 1.80 (s, 3H, CH$_3$), 1.37 (s, 9H, t-Bu).

(2) Synthesis of (S)—N-tert-butoxycarbonyl-β-(1-thyminyl)alanine (Compound 4)

Compound 3 (2.34 g, 5.60 mmol) was dissolved in methanol (40 mL), a 28% ammonia solution (30 mL) was added thereto, and the mixture was stirred at room temperature for 2 hours after sealing. After concentrating the reaction solution, the solution was dissolved in a mixed solution of acetonitrile and water (3:1, 60 mL) and neutralized with an ion-exchange resin (proton form). After removing the ion-exchange resin by filtration, the solution was concentrated under reduced pressure. The resulting residue was suspended in ether (50 mL) and collected by filtration to obtain 1.52 g (86%) of the title compound (Compound 4) as a white powder.

$^1$H NMR (500 MHz, DMSO-$d_6$) δ:13.00 (br s, 1H, COOH), 11.25 (s, 1H, 3-NH), 7.31 (s, 1H, H-6), 7.14 (d, 1H, NH, J=9.0 Hz), 4.31 (ddd, 1H, CH, J=4.8, 9.0, 10.2 Hz), 4.20 (dd, 1H, CH$_2$a, J=4.8, 13.7 Hz), 3.54 (dd, 1H, CH$_2$b, J=10.2, 13.7 Hz), 1.72 (s, 3H, CH$_3$), 1.32 (s, 9H, t-Bu).

(3) Synthesis of (S)—N-tert-butoxycarbonyl-β-(1-thyminyl)alanine Cyanomethyl Ester (Compound 5)

Under an argon atmosphere. Compound 4 (313 mg, 1.0 mmol) was dissolved in acetonitrile (15 mL) and cooled on ice and triethylamine (0.56 mL, 4.0 mmol) and chloroacetonitrile (0.25 mL, 4.0 mmol) were added. The temperature of the reaction solution was returned to room temperature and then the reaction solution was stirred for 22 hours. The reaction solution was concentrated under reduced pressure, then the residue was dissolved in ethyl acetate (70 mL) and washed twice with water (30 mL) and once with saturated brine (30 mL), and the organic layer was dried over sodium sulfate. The solution was concentrated under reduced pressure and the resulting residue was purified by silica gel column chromatography (elution solvent: chloroform-ethanol) to obtain 205 mg (58%) of the title compound (Compound 5) as a white solid.

$^1$H NMR (500 MHz, DMSO-$d_6$) δ:11.31 (s, 1H, 3-NH), 7.50 (d, 1H, NH, J=8.6 Hz), 7.34 (s, 1H, H-6), 5.05 (d, 1H, CH$_2$aCN, J=16.0 Hz), 5.01 (d, 1H, CH$_2$bCN, J=16.0 Hz), 4.47 (ddd, 1H, CH, J=5.2, 9.5, 8.6 Hz), 4.16 (dd, 1H, CH$_2$a, J=5.2, 13.8 Hz), 3.70 (dd, 1H, CH$_2$b, J=9.5, 13.8 Hz), 1.73 (s, 3H, CH$_3$), 1.34 (s, 9H, t-Bu).

(4) Synthesis of (S)-β-(1-thyminyl)alanine Cyanomethyl Ester Hydrochloride (Compound 6)

Under an argon atmosphere, Compound 5 (200 mg, 0.57 mmol) was dissolved in dichloromethane (10 mL) and cooled on ice, and triethyl silane (0.46 mL, 2.9 mmol) and trifluoroacetic acid (0.64 mL, 8.6 mmol) were added. The temperature of the reaction solution was returned to room temperature and the reaction solution was stirred for 4 hours. The reaction solution was concentrated under reduced pressure and then the residue was boiled with toluene three times. Subsequently, a hydrochloric acid/ethyl acetate solution (1 N, 5.0 mL) was added to the residue, the solution was concentrated 5 times under reduced pressure, and trifluoroacetate was replaced with hydrochloride. The resulting white solid was dissolved in an aqueous solution (8.0 mL) of 0.5 N hydrochloric acid, purified by reverse phase silica gel column chromatography (Waters Corp., Sep-Pac Vac C-18 10 g, elution solvent: water-acetonitrile), and freeze-dried to obtain 129 mg (78%) of the title compound (Compound 6) as a white solid.

$^1$H NMR (500 MHz, DMSO-$d_6$) δ:11.42 (s, 1H, 3-NH), 8.49 (br s, 3H, NH3), 7.38 (d, 1H, H-6, J=1.2 Hz), 5.12 (s, 2H, CNCH$_2$), 4.50 (dd, 1H, CH, J=5.8, 6.5 Hz), 4.11 (dd, 1H, CH$_2$a, J=5.8, 14.7 Hz), 4.05 (dd, 1H, CH$_2$b, J=6.5, 14.7 Hz), 1.75 (s, 3H, CH$_3$).

1-2. Synthesis of (S)-γ-(1-thyminyl)homoalanine Cyanomethyl Ester Hydrochloride (HalT Cyanomethyl Ester Derivative: Compound 13)

(1) Synthesis of (S)—N-tert-butoxycarbonyl-γ-hydroxy-homoalanine Benzyl Ester (Compound 8)

Under an argon atmosphere, Compound 7 (1.94 g, 6.00 mmol) was dissolved in tetrahydrofuran (50 mL) and cooled on ice and a BH$_3$-THF/THF solution (1.1 mol/L, 16.4 mL, 18.0 mmol) was slowly added dropwise. The temperature of the reaction solution was returned to room temperature and the reaction solution was stirred for 2.5 hours. The saturated aqueous solution of ammonium chloride (50 mL) was added to the reaction solution and then ethyl acetate (100 mL) was added and the mixture was separated. An organic layer was washed with water (50 mL) and saturated brine (50 mL) and dried over sodium sulfate. The solution was concentrated under reduced pressure and the resulting residue was purified by silica gel column chromatography (elution solvent:

hexane-ethyl acetate) to obtain 1.38 g (74%) of the title compound (Compound 8) as a white solid.

$^1$H NMR (500 MHz, DMSO-$d_6$) δ:7.37-7.32 (m, 5H, Ph), 7.23 (d, 1H, NH, J=7.7 Hz), 5.15 (d, 1H, PhCH$_2$a, J=12.7 Hz), 5.07 (d, 1H, PhCH$_2$b, J=12.7 Hz), 4.59 (t, 1H, OH, J=5.0 Hz), 4.14 (m, 1H, CH), 3.46-3.38 (m, 2H, CH$_2$OH), 1.81 (m, 1H, CH$_2$a), 1.72 (m, 1H, CH$_2$b), 1.37 (s, 9H, t-Bu).

(2) Synthesis of (S)—N-tert-butoxycarbonyl-γ-bromo-homoalanine Benzyl Ester (Compound 9)

Under an argon atmosphere, Compound 8 (890 mg, 2.88 mmol) was dissolved in dichloromethane (40 mL) and cooled on ice, and triphenylphosphine (980 mg, 3.74 mmol) and N-bromosuccinimide (670 mg, 3.74 mmol) were simultaneously added, and the mixture was stirred for 10 minutes with cooling on ice and then for further 1.5 hours at room temperature. The saturated aqueous solution of sodium bicarbonate (50 mL) was added to the reaction solution and then chloroform (70 mL) was added and the mixture was separated. An organic layer was washed with water (50 mL) and saturated brine (50 mL) and dried over sodium sulfate. The solution was concentrated under reduced pressure and the resulting residue was purified by silica gel column chromatography (elution solvent: hexane-ethyl acetate) to obtain 700 mg (65%) of the title compound (Compound 9) as a white crystal.

$^1$H NMR (500 MHz, DMSO-$d_6$) δ:7.41 (d, 1H, NH, J=8.0 Hz), 7.37-7.32 (m, 5H, Ph), 5.16 (d, 1H, PhCH$_2$a, J=12.5 Hz), 5.10 (d, 1H, PhCH$_2$b, J=12.5 Hz), 4.18 (m, 1H, CH), 3.56 (m, 1H, BrCH$_2$a), 3.49 (m, 1H, BrCH$_2$b), 2.20-2.12 (m, 2H, CH$_2$), 1.37 (s, 9H, t-Bu).

(3) Synthesis of (S)—N-tert-butoxycarbonyl-γ-(N3-benzoyl-1-thyminyl)homoalanine Benzyl Ester (Compound 10)

Under an argon atmosphere, Compound 9 (610 mg, 1.64 mmol) and N3-benzoylthymine (Compound 2) (566 mg, 2.46 mmol) were dissolved in dimethylformamide (25 mL), potassium carbonate powder (340 mg, 2.46 mmol) and tetrabutylammonium iodide (59 mg, 0.16 mmol) were added, and the mixture was heated at 80° C. for 30 minutes and stirred. The reaction solution was cooled to room temperature, and then ethyl acetate (150 mL) was added, and the organic layer was washed four times with water (50 mL) and once with saturated brine (50 mL) and dried over sodium sulfate. The solution was concentrated under reduced pressure and the resulting residue was purified by silica gel column chromatography (elution solvent: hexane-ethyl acetate) to obtain 726 mg (85%) of the title compound (Compound 10) as a white foam.

$^1$H NMR (500 MHz, DMSO-$d_6$) δ:7.94 (m, 2H, Bz), 7.78 (m, 1H, Bz), 7.68 (s, 1H, H-6), 7.58 (m, 2H, Bz), 7.45 (br d, 1H, NH, J=8.1 Hz), 7.36-7.32 (m, 5H, Bn), 5.14 (d, 1H, PhCH$_2$a, J=12.6 Hz), 5.10 (d, 1H, PhCH$_2$b, J=12.6 Hz), 4.10 (m, 1H, CH), 3.82 (m, 1H, CH$_2$a), 3.76 (m, 1H, CH$_2$b), 2.13 (m, 1H, CH$_2$a), 1.96 (m, 1H, CH$_2$b), 1.81 (s, 3H, CH$_3$), 1.37 (s, 9H, t-Bu).

(4) Synthesis of (S)—N-tert-butoxycarbonyl-γ-(1-thyminyl) Homoalanine (Compound 11)

Compound 10 (720 mg, 1.38 mmol) was dissolved in a mixed solution of dioxane-water (3:2, 30 mL), an aqueous solution of 1N sodium hydroxide (6.9 mL) was added, and the mixture was stirred at room temperature for 20 hours. After neutralizing the reaction solution with ion-exchange resin (proton form), the ion-exchange resin was removed by filtration and the solution was concentrated under reduced pressure. The residue was boiled with toluene three times and the resulting residue was purified by silica gel column chromatography (elution solvent: chloroform-ethanol) to obtain 441 mg (98%) of the title compound (Compound 11) as a white solid.

$^1$H NMR (500 MHz, DMSO-$d_6$) δ:12.64 (br s, 1H, COOH), 11.23 (s, 1H, 3-NH), 7.41 (s, 1H, H-6), 7.19 (br d, 1H, NH, J=8.0 Hz), 3.87 (m, 1H, CH), 3.70-3.63 (m, 2H, CH$_2$), 2.02 (m, 1H, CH$_2$a), 1.83 (m, 1H, CH$_2$b), 1.73 (s, 3H, CH), 1.39 (s, 9H, t-Bu).

(5) Synthesis of (S)—N-tert-butoxycarbonyl-γ-(1-thyminyl)homoalanine Cyanomethyl Ester (Compound 12)

Under an argon atmosphere, Compound 11 (430 mg, 1.31 mmol) was dissolved in acetonitrile (20 mL) and cooled on ice, and triethylamine (1.09 mL, 7.86 mmol) and chloroacetonitrile (0.25 mL, 3.93 mmol) were added. The temperature of the reaction solution was returned to room temperature and then the reaction solution was stirred for 18 hours. The reaction solution was concentrated under reduced pressure, then the residue was dissolved in ethyl acetate (100 mL) and washed twice with water (35 mL) and once with saturated brine (35 mL), and the organic layer was dried over sodium sulfate. The solution was concentrated under reduced pressure and the resulting residue was purified by silica gel column chromatography (elution solvent: chloroform-ethanol) to obtain 266 mg (55%) of the title compound (Compound 12) as a white foam.

$^1$H NMR (500 MHz, DMSO-$d_6$) δ:11.23 (s, 1H, 3-NH), 7.52 (br d, 1H, NH, J=7.8 Hz), 7.41 (s, 1H, H-6), 5.00 (s, 2H, CH$_2$CN), 4.06 (m, 1H, CH), 3.69 (m, 2H, CH$_2$), 2.06 (m, 1H, CH$_2$a), 1.87 (m, 1H, CH$_2$b), 1.74 (s, 3H, CH$_3$), 1.40 (s, 9H, t-Bu).

(6) Synthesis of (S)-γ-(1-thyminyl)homoalanine Cyanomethyl Ester Hydrochloride (Compound 13)

Under an argon atmosphere, Compound 12 (264 mg, 0.72 mmol) was dissolved in dichloromethane (8.0 mL) and cooled on ice, and triethylsilane (0.35 mL, 2.16 mmol) and trifluoroacetic acid (0.53 mL, 7.2 mmol) were added. The temperature of the reaction solution was returned to room temperature and the reaction solution was stirred for 3 hours. The reaction solution was concentrated under reduced pressure and then the residue was boiled with toluene three times. Subsequently, a solution of hydrochloric acid solution in ethyl acetate (1N, 5.0 mL) was added to the residue, the solution was concentrated 5 times under reduced pressure, and trifluoroacetate was replaced with hydrochloride. The resulting white solid was dissolved in an aqueous solution (8.0 mL) of 0.5 N hydrochloric acid, purified by reverse phase silica gel column chromatography (Waters Corp., Sep-Pac Vac C-18 10 g, elution solvent: water-acetonitrile), and freeze-dried to obtain 133 mg (61%) of the title compound (Compound 13) as a white foam.

$^1$H NMR (500 MHz, DMSO-$d_6$) δ:11.32 (br s, 1H, 3-NH), 8.50 (br s, 3H, NH3), 7.48 (d, 1H, H-6, J=1.3 Hz), 5.16 (d, 1H, CH$_2$aCN, J=16.0 Hz), 5.12 (d, 1H, CH$_2$bCN, J=16.0 Hz), 4.22 (t, 1H, CH, J=6.7 Hz), 3.79 (m, 2H, CH$_2$), 2.17 (n, 1H, CH$_2$a), 2.06 (m, 1H, CH$_2$b), 1.76 (s, 3H, CH$_3$).

2. Production of NBA-Acylated tRNA

Aminoacylated tRNAs were prepared by using the AlaT cyanomethyl ester derivative (hereinafter referred to as "AlaT-CME") and HalT cyanomethyl ester derivative (hereinafter referred to as "HalT-CME") synthesized as 1 described above. The aminoacylation reaction was conducted with a ribozyme that catalyzes the aminoacylation reaction. The procedure and results are described below in detail.

2-1. eFx and Preparation of tRNA

Enhanced flexizyme eFx was used as the ribozyme that catalyzes the aminoacylation reaction. The eFx is a ribozyme that uses a cyanomethyl ester derivative of phenylalanine (hereinafter referred to as "Phe-CME") as a substrate, and condenses phenylalanine with tRNA having the sequence of ACCA or GCCA at the 3' terminus (Murakami et al., Nat. Meth., Vol. 3, pp. 357-359, 2006). The $tRNA_{CUA}$, which has an anticodon (CUA) to an amber codon (TAG), was used as the tRNA. For the evaluation of efficiency of the aminoacylation reaction, the tRNA analog microhelix (hereinafter referred to as "mihx") was used instead of the $tRNA_{CUA}$. The mihx is a model substrate of the eFx mimicking only the 3' terminus portion of tRNA with which the 3' terminus (AGGU, underlined) of the eFx interacts upon the aminoacylation reaction; has a 3' terminus sequence (GCCA, underlined) having the same effect as the 3' terminus sequence (ACCA, underlined) of tRNA; and aminoacylated similarly to tRNA.

[Formula 1]
eFx (SEQ ID NO: 1):
GGAUCGAAAGAUUUCCGCGGCCCCGAAAGGGGAUUAGCGUU<u>AGGU</u>

[Formula 2]
$tRNA_{CUA}$ (SEQ ID NO: 2):
GGGAGAGUAGUUCAAUGGUAGAACGUCGGUCUcuaAAACCGAGCG
UUGAGGGUUCGAUUCCUUUCUCUCCC<u>ACCA</u> wherein cua is the anticodon to the amber codon.

[Formula 3]
mihx (SEQ ID NO: 3):
GGCUCUGUUCGCAGAGCC<u>GCCA</u>

The eFx, $tRNA_{CUA}$ and mihx were all synthesized by in vitro transcription. 250 nM template DNA, 40 mM Tris (pH 8.0), 2 mM spermidine, 30 mM MgClhd 2, 10 mM dithiothreitol, 25 mM each ribonucleotide triphosphates, and 1 µg/ml T7 RNA polymerase (all final concentration) were mixed into 1 mL aqueous solution to prepare the reaction solution. The synthesis of $tRNA_{CUA}$ and mihx was conducted by adding final concentration 20 mM guanosine monophosphate to the reaction solution. After incubation for 3 hours at 37° C., the reaction solution was concentrated by ethanol precipitation and then polyacrylamide gel electrophoresis (PAGE) with 6 M urea was conducted. The band of the synthesized RNA was cut out from the gel after the electrophoresis, the RNA was eluted from the gel piece cut out with a TE buffer solution (10 mM Tris-HCl pH 8.0, 1 mM EDTA), and the RNA was purified by ethanol precipitation. The purified RNA was dissolved in purified water and prepared all at 250 µM.

2-2. Aminoacylation of tRNA by Flexizyme eFx

The aminoacylation reaction was then conducted.

(1) Aminoacylation of Mihx Using AlaT-CME

25 µM eFx, 25 µM mihx, 50 mM HEPES (pH 7.5), 600 mM $MgCl_2$, and 50 mM AlaT-CME (all final concentration) were mixed into 40 µL aqueous solution. After reacting the mixture on ice for 1 to 12 hours, the mixture was purified by ethanol precipitation to obtain the aminoacylated product of mihx with AlaT (hereinafter referred to as "mihx-AlaT"). Purified mihx-AlaT was dissolved in 1 µL of 10 mM sodium acetate (pH 5.3).

(2) Aminoacylation of Mihx Using HalT-CME

The aminoacylation reaction was conducted similarly to (1) described above except that HalT-CME was used instead of AlaT-CME to obtain the aminoacylated product of mihx with HalT (hereinafter referred to as "mihx-HalT").

(3) Aminoacylation of Mihx Using Phe-CME (Positive Control)

The aminoacylation reaction was conducted similarly to (1) described above except that Phe-CME was used instead of AlaT-CME to obtain the aminoacylated product of mihx with phenylalanine (Phe) (hereinafter referred to as "mihx-Phe").

The mihx-AlaT, mihx-HalT, and mihx-Phe were subjected to the electrophoresis using a polyacrylamide gel under acidic conditions (6M urea, 20% acrylamide-bis acrylamide, 50 mM sodium acetate, pH 5.3) and a 50 mM sodium acetate buffer solution at pH 5.3. After the staining of the acrylamide gel after the electrophoresis with ethidium bromide, the bands of the RNAs were photographed and quantified with GelDoc (BioRad).

Figure 6:
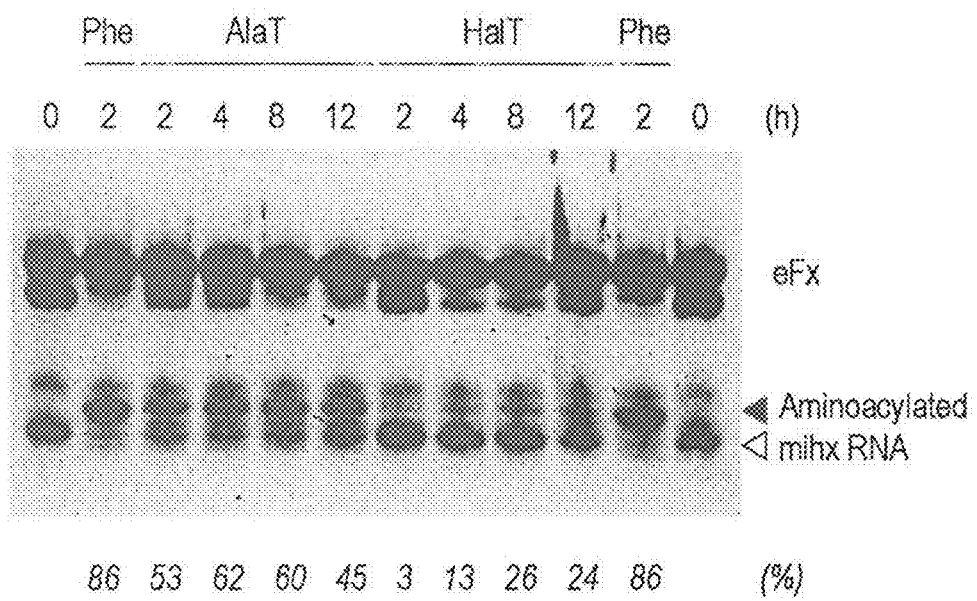
FIG. 6 illustrates the production of nucleobase amino acid (NBA)-aminoacylated tRNAs with an eFx.
Figure 7:
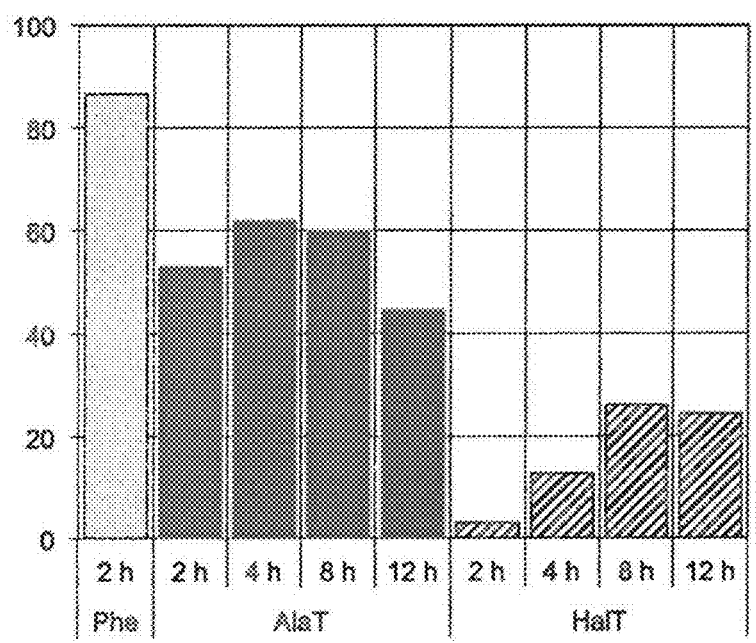
FIG. 7 is a graph that compares the production efficiencies of nucleobase amino acid (NBA)-aminoacylated tRNAs with an eFx.

The results are illustrated in FIGS. 6 and 7. FIG. 6 is the result of the electrophoresis. The number above each lane indicates the hours of the aminoacylation reaction. The number below each lane indicates the aminoacylation efficiency calculated from the ratio of the band of unreacted mihx (white arrow) and the band of aminoacylated mihx (black arrow). Aminoacylation of mihx (white arrow) increases the molecular weight and causes the upward band-shift (black arrow). The bands observed above them are attributed to eFx or degradation products thereof. FIG. 7 is a graph of the aminoacylation efficiency calculated from the result of FIG. 6. These results demonstrated that tRNA can be aminoacylated with either of the NBAs AlaT and HalT using eFx although the efficiency is lower than that with natural amino acids.

2-3. Aminoacylation of tRNA with Split eFx

A test was conducted to examine whether a similar aminoacylation reaction can be performed using a chemically synthesized eFx instead of an eFx prepared by in vitro transcription in 2-2 described above. The full length eFx and an eFx consisting of the following two RNA molecules (hereinafter referred to as "split eFx") were chemically synthesized. Furthermore, the 3' terminus of the upstream-split eFx and the 5' terminus of downstream-split eFx in the split eFx were biotinylated.

[Formula 4]
Upstream-split eFx (SEQ ID NO: 4):
GGAUCGAAAGAUUUCCGCGGCCCCG

[Formula 5]
Downstream-split eFx (SEQ ID NO: 5):
CGGGGAUUAGCGUU<u>AGGU</u>

Schematic drawings of the full length eFx and the split eFx are shown in FIG. 8 (a) and FIG. 8 (b), respectively. The portions in frame indicate mihx.

The aminoacylation reaction of mihx with phenylalanine (Phe) was conducted similarly to 2-2 (3) except that the chemically synthesized full length eFx and the split eFx were used. After the electrophoresis of the reaction products in an acid polyacrylamide gel, ethidium bromide staining was conducted and RNA bands were observed.

Figure 9:
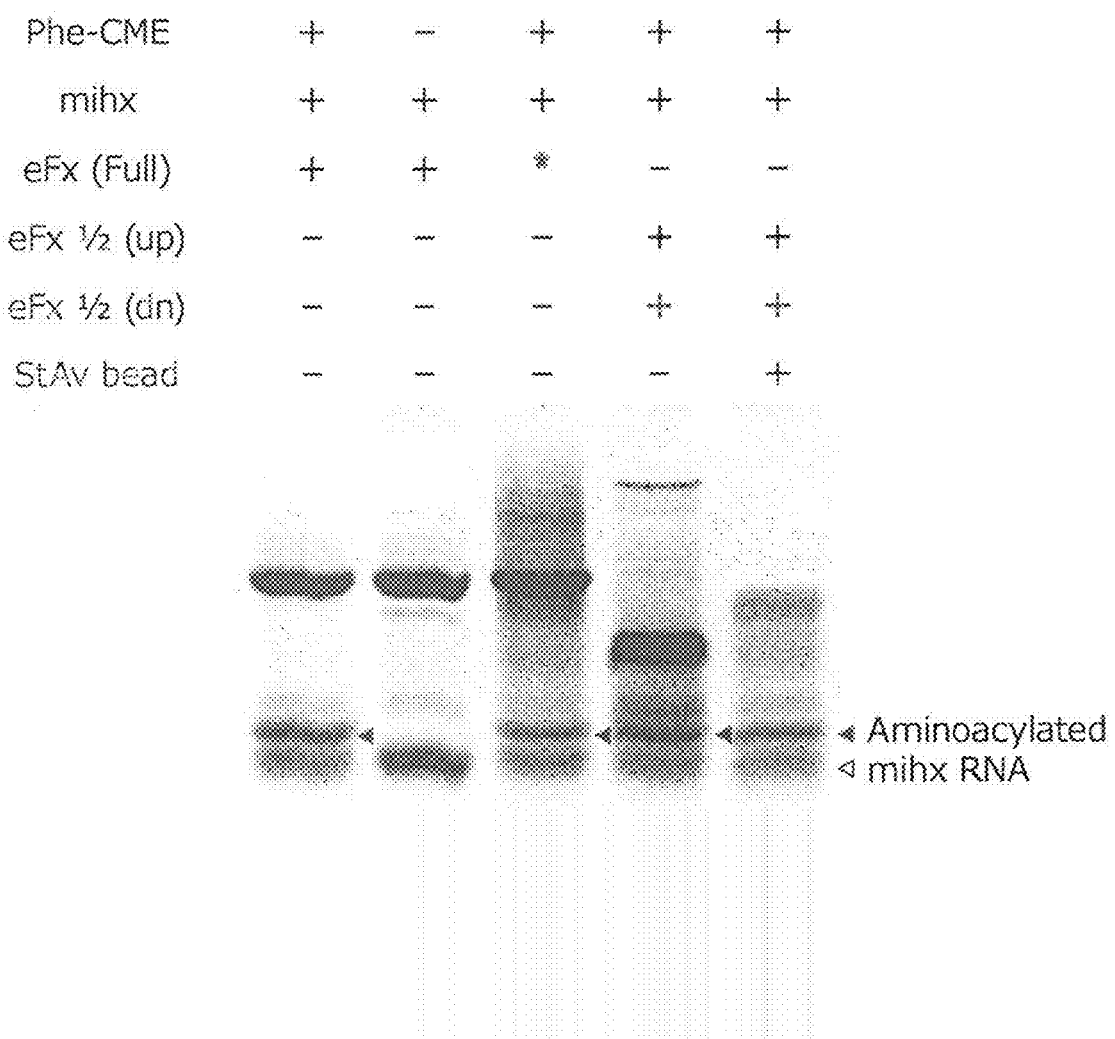
FIG. 9 illustrates the confirmation of the aminoacylation reaction of tRNA with a split eFx.

The result is illustrated in FIG. 9. The aminoacylation of mihx with Phe was confirmed in either of the cases in which the chemically synthesized full length eFx was used (Lane 3, the sign "*" in the figure indicates the addition of the chemically synthesized eFx (that is, with no 5'-terminal phosphate group)) and in which the chemically synthesized split eFx was used (Lane 4) similarly to the case in which the eFx synthesized by in vitro transcription was used (Lane 1). These results demonstrated that the 5'-terminal phosphate group of eFx is not necessary for the aminoacylation reaction, and the aminoacylation reaction can be performed using either of the chemically synthesized full length eFx and split eFx, similarly to that using the eFx synthesized by in vitro transcription. It was also confirmed that the biotinylated and chemically synthesized split eFx can be removed from reaction products by purification using streptavidin beads (Lane 5).

2-4. Aminoacylation of tRNA with Split dFx

Also, as a flexizyme other than eFx, dinitrobenzyl flexizyme (dFx) consisting of two RNA molecules: upstream-split dFx (GGAUCGAAAGAUUUCCGCAUCCCCG: SEQ ID NO: 7) and downstream-split dFx (CGGGUACAUG-GCGUUAGGU: SEQ ID NO: 8) (hereinafter referred to as "split dFx") was chemically synthesized and tested for the aminoacylation activity. Schematic drawings of the full length dFx and the split dFx are shown in FIG. 11 (a) and FIG. 11 (b), respectively. The portions in frame indicate mihx.

The full length dFx was prepared by in vitro transcription and the split dFx was prepared by chemical synthesis. The aminoacylation reaction of mihx with phenylalanine (Phe) was conducted similarly to 2-3 except that the full length dFx (SEQ ID NO: 9) and the split dFx were used instead of the full length eFx and the split eFx and a dinitrobenzyl ester derivative of phenylalanine (Phe-DBE) was used instead of Phe-CME.

Figure 12:
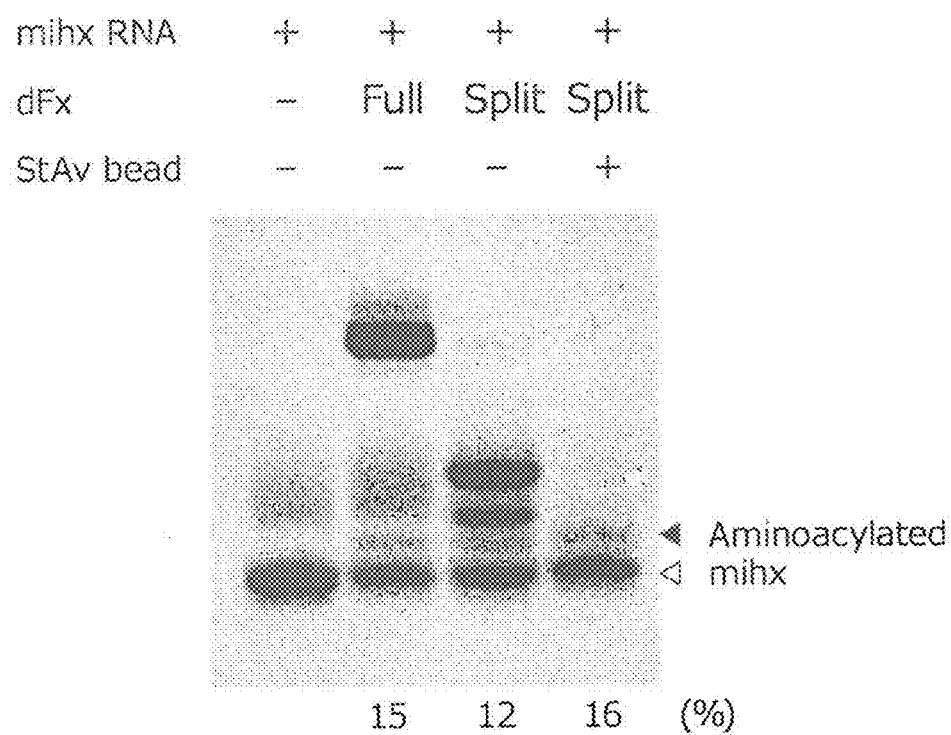
FIG. 12 illustrates the confirmation of the aminoacylation reaction of tRNA with a split dFx.

The result is illustrated in FIG. 12. The number below each lane indicates the aminoacylation efficiency calculated from the ratio of the band of unreacted mihx (white arrow) and the band of aminoacylated mihx (black arrow). This result demonstrated that the split dFx (Lane 3) has the aminoacylation activity at the efficiency equivalent to the full length dFx (Lane 2). It was also confirmed that the biotinylated and chemically synthesized split dFx can be removed from reaction products by purification using streptavidin beads (Lane 4).

As seen above, it was demonstrated for the first time that flexizyme has the aminoacylation activity, regardless of the presence or absence of the 5'-terminal phosphate group, and that flexizyme can be divided into two RNA molecules and prepared by chemical synthesis easily and at low cost. Furthermore, it was confirmed that biotin modification can be easily introduced into the flexizyme consisting of two RNA molecules by chemical synthesis and the purification efficiency after the aminoacylation reaction can be improved thereby.

3. Incorporation of tRNA-NBA into Ribosome

The aminoacylation product of tRNA$_{CUA}$ with AlaT or Hal-T (hereinafter referred to as "tRNA-AlaT" or "tRNA-HalT", respectively) was prepared using tRNA$_{CUA}$ instead of mihx in 2-2 (1) described above, and it was tested whether the NBA-acylated tRNA is incorporated into the ribosome similarly to the normal tRNAs acylated with natural amino acids.

3-1. Preparation of Template DNA

A gene (SEQ ID NO: 6) in which the amber codon is inserted upstream of the green fluorescent protein (GFP) gene was prepared. As illustrated below, this gene includes, from upstream, a T7 promoter (underlined), a SD sequence (double-underlined), a start codon (in single line frame), an amber codon (in double line frame), a HRV3C protease cleavage sequence (in dashed line frame), a GFP gene sequence (in dashed dot line frame) and an ochre codon (in frame with shade) and contains one glycine codon between the start codon and the amber codon and two glycine codons between the amber codon and the HRV3C protease cleavage sequence. The double-stranded DNA of the gene was prepared at a concentration of 0.04 μg/μL and used as template DNA for the translation reaction with the following ribosome.

Formula 6

GTAATACGACTCACTATAGGGTTAACTTTAACAAGGAGAAAAACATGGGTtagGGCGGCCTT

GAAGTGCTCTTCCAAGGTCCTGTGAGCAAGGGCGAGGAGCTGTTCACCGGGGTGGTGCCC

ATCCTGGTCGAGCTGGACGGCGACGTAAACGGCCACAAGTTCAGCGTGTCCGGCGAGGGC

GAGGGCGATGCCACCTACGGCAAGCTGACCCTGAAGTTCATCTGCACCACCGGCAAGCTG

CCCGTGCCCTGGCCCACCCTCGTGACCACCTTGACCTACGGCGTGCAGTGCTTCGCCCGC

TACCCCGACCACATGAAGCAGCACGACTTCTTCAAGTCCGCCATGCCCGAAGGCTACGTC

CAGGAGCGCACCATCTTCTTCAAGGACGACGGCAACTACAAGACCCGCGCCGAGGTGAA

GTTCGAGGGCGACACCCTGGTGAACCGCATCGAGCTGAAGGGCATCGACTTCAAGGAGGA

CGGCAACATCCTGGGGCACAAGCTGGAGTACAACTACAACAGCCACAAGGTCTATATC

ACCGCCGACAAGCAGAAGAACGGCATCAAGGTGAACTTCAAGACCCGCCACAACATCG

AGGACGGCAGCGTGCAGCTCGCCGACCACTACCAGCAGAACACCCCCATCGGCGACGG

CCCCGTGCTGCTGCCCGACAACCACTACCTGAGCACCCAGTCCAAGCTGAGCAAAGACC

CCAACGAGAAGCGCGATCACATGGTCCTGCTGGAGTTCGTGACCGCCGCCGGGATCACT

CTCGGCATGGACGAGCTGTACAAG TAA GAGCTCTGTG

3-2. Translation of Template DNA with Ribosome

4 µL of Solution A and 3 µL of Solution B attached to the PURExpress kit (New England Biolab Inc.), 1 µL of purified water, 1 µL of the tRNA-AlaT or tRNA-HalT solution, and 1 µl of 0.04 µg/µl template DNA were mixed to become 10 µL and the translation reaction was performed. Solution A and Solution B described above contain the translation initiation factor, the translation elongation factor, the translation termination factor, aminoacylated tRNA synthetase, T7 RNA polymerase, ribosome, 20 natural amino acids, total tRNA from *Escherichia coli*, deoxyribonucleotide triphosphate, etc. necessary for transcription, translation, and energy reproduction, and a protein of interest can be synthesized by mixing them with a template DNA. After the reaction for 3 hours at 37° C., 9 µL of the reaction solution was transferred to 384-well plate (Greiner Bio-One International GmbH) and the fluorescence of synthesized GFP was measured with a plate reader (Tecan Group Ltd.).

Figure 10:
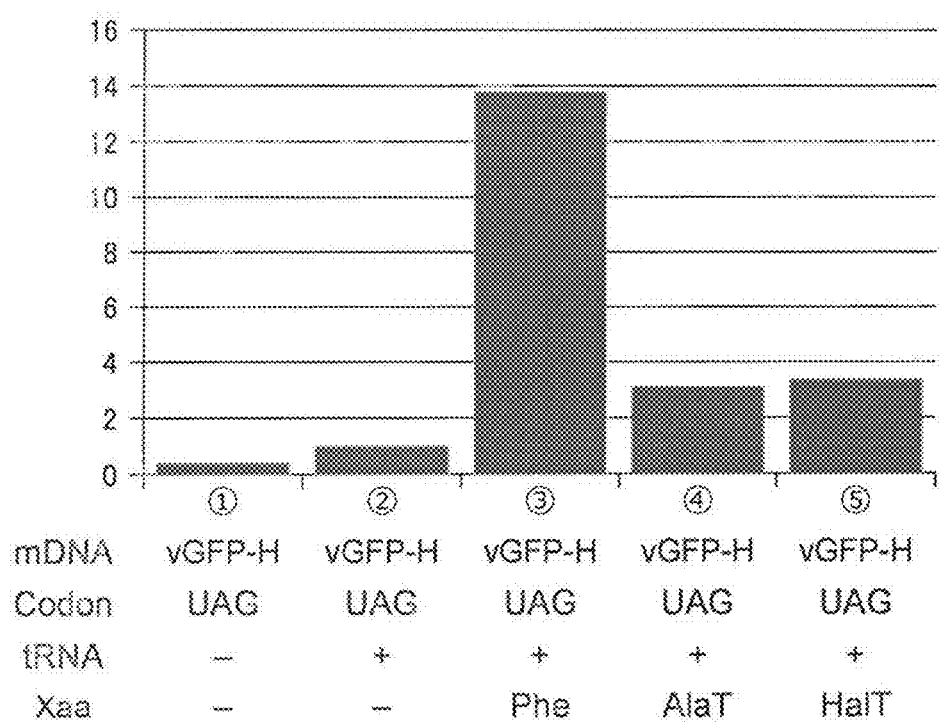
FIG. 10 illustrates the confirmation of synthesis of GFP having a nucleobase amino acid (NBA) introduced.

The result is illustrated in FIG. 10. The graph illustrates, sequentially from the left, the GFP fluorescence intensity in the reaction when (1) only the template DNA was added (negative control): (2) the template DNA and $tRNA_{CUA}$ that was not aminoacylated were added (negative control); (3) the template DNA and $tRNA_{CUA}$ aminoacylated with Phe were added (positive control); (4) the template DNA and tRNA-AlaT were added: and (5) the template DNA and tRNA-HalT were added (values relative to (2)). The GFP fluorescence intensity in (4) and (5) was clearly increased in comparison with the negative controls. Thus, it was confirmed that suppression occurred with either of tRNA-AlaT and tRNA-HalT to synthesize GFP into which AlaT or HalT was incorporated. The lower GFP fluorescence intensity in (4) and (5) than in (3) is understood to be result from combined effects of the difference in the efficiency of tRNA aminoacylation with amino acids, the difference in the efficiency of incorporation of aminoacylated tRNAs into ribosome, etc.

From the foregoing results, it was demonstrated that a protein into which an NBA is introduced at a desired position can be synthesized with a ribosomal translation system.

The invention claimed is:

1. A method for synthesizing a protein, comprising the steps of:
 providing an mRNA having a modified codon inserted at a desired position downstream of a start codon; and
 translating the mRNA into a protein in the presence of a tRNA acylated with a nucleobase amino acid (NBA) and recognizing the modified codon, wherein the NBA is an amino acid having a nucleobase as a side chain thereof, the nucleobase is selected from the group consisting of thymine (T), uracil (U), and derivatives thereof.

2. The method according to claim 1, further comprising the step of preparing the tRNA acylated with the NBA with a ribozyme that catalyzes the aminoacylation reaction of the tRNA.

3. The method according to claim 2, wherein the ribozyme is a flexizyme consisting of the nucleotide sequence of SEQ ID NO:1.

4. The method according to claim 2, wherein the ribozyme consists of one or more RNA molecules having no 5'-terminal phosphate group.

5. The method according to claim 2, wherein the ribozyme consists of two RNA molecules.

6. The method according to claim 5, wherein the ribozyme consists of the following two RNA molecules:

(1)
                                              (SEQ ID NO: 4)
GGAUCGAAAGAUUUCCGCGGCCCCG
and (2)
                                              (SEQ ID NO: 5)
CGGGGAUUAGCGUUAGGU.

7. The method according to claim 1, wherein the modified codon is an amber codon.

8. A cell-free protein synthesis system for synthesizing a protein, comprising:
 (1) a nucleobase amino acid (NBA), wherein the NBA is an amino acid having a nucleobase as a side chain thereof, the nucleobase is selected from the group consisting of thymine (T), uracil (U), and derivatives thereof,
 (2) a tRNA that recognizes a modified codon, and
 (3) a ribozyme that catalyzes the aminoacylation reaction of the tRNA.

9. The cell-free protein synthesis system according to claim 8, wherein the ribozyme is a flexizyme consisting of the nucleotide sequence of SEQ ID NO:1.

10. The cell-free protein synthesis system according to claim 8, wherein the ribozyme consists of one or more RNA molecules having no 5'-terminal phosphate group.

11. The cell-free protein synthesis system according to claim 8, wherein the ribozyme consists of two RNA molecules.

12. The cell-free protein synthesis system according to claim 11, wherein the two RNA molecules are (1)
                                              (SEQ ID NO: 4)
GGAUCGAAAGAUUUCCGCGGCCCCG
and (2)
                                              (SEQ ID NO: 5)
CGGGGAUUAGCGUUAGGU.

13. The cell-free protein synthesis system according to claim 8, wherein the modified codon is an amber codon.

* * * * *

UNITED STATES PATENT AND TRADEMARK OFFICE
CERTIFICATE OF CORRECTION

PATENT NO. : 10,711,273 B2
APPLICATION NO. : 15/579841
DATED : July 14, 2020
INVENTOR(S) : Kato et al.

Page 1 of 1

It is certified that error appears in the above-identified patent and that said Letters Patent is hereby corrected as shown below:

In the Specification

Column 5, Line 7: Please correct "SEQ ID NO" to read -- SEQ ID NO: --

Column 5, Line 14: Please correct "NO:3 and" to read -- NO:3) and --

Column 14, Line 13: Please correct "CH)" to read -- $CH_3$) --

Colman 14, Line 66: Please correct "(n," to read -- (m, --

Column 15, Line 45: Please correct "MgClhd 2," to read -- $MgCl_2$, --

Signed and Sealed this
Fifteenth Day of December, 2020

Andrei Iancu
*Director of the United States Patent and Trademark Office*

SEQUENCE LISTING

```
<160> NUMBER OF SEQ ID NOS: 9

<210> SEQ ID NO 1
<211> LENGTH: 45
<212> TYPE: RNA
<213> ORGANISM: artificial
<220> FEATURE:
<223> OTHER INFORMATION: Ribozyme eFx

<400> SEQUENCE: 1
ggaucgaaag auuuccgcgg ccccgaaagg ggauuagcgu uaggu          45

<210> SEQ ID NO 2
<211> LENGTH: 75
<212> TYPE: RNA
<213> ORGANISM: artificial
<220> FEATURE:
<223> OTHER INFORMATION: tRNA comprising sequence recognizing amber stop
      codon (tRNACUA)

<400> SEQUENCE: 2
gggagaguag uucaauggua gaacgucggu cucuaaaacc gagcguugag gguucgauuc      60
cuuucucucc cacca                                                      75

<210> SEQ ID NO 3
<211> LENGTH: 22
<212> TYPE: RNA
<213> ORGANISM: artificial
<220> FEATURE:
<223> OTHER INFORMATION: tRNA model substrate (mihx)

<400> SEQUENCE: 3
ggcucuguuc gcagagccgc ca                                              22

<210> SEQ ID NO 4
<211> LENGTH: 25
<212> TYPE: RNA
<213> ORGANISM: artificial
<220> FEATURE:
<223> OTHER INFORMATION: upstream ribozyme eFX-up

<400> SEQUENCE: 4
ggaucgaaag auuuccgcgg ccccg                                           25
```

<210> SEQ ID NO 5
<211> LENGTH: 18
<212> TYPE: RNA
<213> ORGANISM: artificial
<220> FEATURE:
<223> OTHER INFORMATION: downstream ribozyme eFx-down

<400> SEQUENCE: 5
cggggauuag cguuaggu                                                 18

<210> SEQ ID NO 6
<211> LENGTH: 810
<212> TYPE: DNA
<213> ORGANISM: artificial
<220> FEATURE:
<223> OTHER INFORMATION: DNA constructing gene expressing GFP

<400> SEQUENCE: 6
gtaatacgac tcactatagg gttaacttta acaaggagaa aaacatgggt tagggcggcc     60
ttgaagtgct cttccaaggt cctgtgagca agggcgagga gctgttcacc ggggtggtgc    120
ccatcctggt cgagctggac ggcgacgtaa acggccacaa gttcagcgtg tccggcgagg    180 gcgaggggcga tgccacctac ggcaagctga ccctgaagtt catctgcacc accggcaagc    240
tgcccgtgcc ctggcccacc ctcgtgacca ccttgaccta cggcgtgcag tgcttcgccc    300
gctaccccga ccacatgaag cagcacgact tcttcaagtc cgccatgccc gaaggctacg    360
tccaggagcg caccatcttc ttcaaggacg acggcaacta caagacccgc gccgaggtga    420
agttcgaggg cgacaccctg gtgaaccgca tcgagctgaa gggcatcgac ttcaaggagg    480
acggcaacat cctggggcac aagctggagt acaactacaa cagccacaag gtctatatca    540
ccgccgacaa gcagaagaac ggcatcaagg tgaacttcaa gacccgccac aacatcgagg    600
acggcagcgt gcagctcgcc gaccactacc agcagaacac ccccatcggc gacggccccg    660
tgctgctgcc cgacaaccac tacctgagca cccagtccaa gctgagcaaa gaccccaacg    720
agaagcgcga tcacatggtc ctgctggagt tcgtgaccgc cgccgggatc actctcggca    780
tggacgagct gtacaagtaa gagctctgtg                                    810

<210> SEQ ID NO 7
<211> LENGTH: 25
<212> TYPE: RNA
<213> ORGANISM: artificial
<220> FEATURE:
<223> OTHER INFORMATION: upstream ribozyme dFX-up

<400> SEQUENCE: 7
ggaucgaaag auuuccgcau ccccg                                         25

<210> SEQ ID NO 8
<211> LENGTH: 19
<212> TYPE: RNA
<213> ORGANISM: artificial
<220> FEATURE:
<223> OTHER INFORMATION: downstream ribozyme dFx-down

<400> SEQUENCE: 8
cggguacaug gcguuaggu                                                19

<210> SEQ ID NO 9
<211> LENGTH: 46
<212> TYPE: RNA
<213> ORGANISM: artificial
<220> FEATURE:

```
<223> OTHER INFORMATION: Ribozyme dFx

<400> SEQUENCE: 9
ggaucgaaag auuuccgcau ccccgaaagg guacauggcg uuaggu                    46
```